United States Patent
Bertges et al.

(10) Patent No.: US 12,205,278 B2
(45) Date of Patent: Jan. 21, 2025

(54) METHOD AND APPARATUS FOR ANALYZING AORTIC ANEURYSMS AND ENDOLEAKS IN COMPUTED TOMOGRAPHY SCANS

(71) Applicant: The University of Vermont and State Agricultural College, Burlington, VT (US)

(72) Inventors: Daniel Bertges, South Burlington, VT (US); Safwan Wshah, Burlington, VT (US); Christopher S. Morris, South Hero, VT (US); Sage Hahn, Burlington, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 583 days.

(21) Appl. No.: 17/602,164

(22) PCT Filed: Apr. 8, 2020

(86) PCT No.: PCT/US2020/027142
§ 371 (c)(1),
(2) Date: Oct. 7, 2021

(87) PCT Pub. No.: WO2020/210278
PCT Pub. Date: Oct. 15, 2020

(65) Prior Publication Data
US 2022/0215536 A1    Jul. 7, 2022

Related U.S. Application Data

(60) Provisional application No. 62/830,982, filed on Apr. 8, 2019.

(51) Int. Cl.
*G06T 7/10* (2017.01)
*A61B 6/03* (2006.01)
(Continued)

(52) U.S. Cl.
CPC .......... *G06T 7/0012* (2013.01); *A61B 6/032* (2013.01); *A61B 6/504* (2013.01); *G06F 18/214* (2023.01);
(Continued)

(58) Field of Classification Search
CPC .......... G06T 7/0012; G06T 7/62; G06T 7/10; G06T 7/70; G16H 50/20; G16H 30/40;
(Continued)

(56) References Cited

U.S. PATENT DOCUMENTS

| 7,324,675 B2 * | 1/2008 | Raman | A61B 5/02007 |
| | | | 382/128 |
| 2005/0180621 A1 * | 8/2005 | Raman | A61B 5/1076 |
| | | | 382/128 |

(Continued)

FOREIGN PATENT DOCUMENTS

CN    109671076 A * 4/2019 .......... G06T 7/0012

OTHER PUBLICATIONS

PCT/US2020/027142, Jun. 23, 2020, International Search Report and Written Opinion.
(Continued)

*Primary Examiner* — Sheela C Chawan
(74) *Attorney, Agent, or Firm* — Wolf, Greenfield & Sacks, P.C.

(57) ABSTRACT

Techniques for diagnosing a patient having an AAA. The techniques include using a computer hardware processor to perform: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, a
(Continued)

diagnosis of the patient, the diagnosis including information identifying at least one condition (e.g., an endoleak, an AAA rupture) of the patient.

20 Claims, 22 Drawing Sheets

(51) Int. Cl.
| | | |
|---|---|---|
| A61B 6/50 | (2024.01) | |
| G06F 18/214 | (2023.01) | |
| G06F 18/2415 | (2023.01) | |
| G06T 7/00 | (2017.01) | |
| G06T 7/62 | (2017.01) | |
| G06T 7/70 | (2017.01) | |
| G06V 10/75 | (2022.01) | |
| G06V 10/764 | (2022.01) | |
| G06V 10/82 | (2022.01) | |
| G16H 30/40 | (2018.01) | |
| G16H 50/20 | (2018.01) | |

(52) U.S. Cl.
CPC ............ *G06F 18/2415* (2023.01); *G06T 7/10* (2017.01); *G06T 7/62* (2017.01); *G06T 7/70* (2017.01); *G06V 10/751* (2022.01); *G06V 10/764* (2022.01); *G06V 10/82* (2022.01); *G16H 30/40* (2018.01); *G16H 50/20* (2018.01); *G06T 2207/10081* (2013.01); *G06T 2207/20081* (2013.01); *G06T 2207/20084* (2013.01); *G06T 2207/30101* (2013.01); *G06V 2201/03* (2022.01)

(58) Field of Classification Search
CPC .... G06V 10/82; G06V 10/751; G06V 10/764; G06F 18/214; G06F 18/2415; A61B 6/032; A61B 3/504
USPC .................................................. 382/131, 100
See application file for complete search history.

(56) References Cited

U.S. PATENT DOCUMENTS

| | | |
|---|---|---|
| 2006/0034508 A1 | 2/2006 | Zhou et al. |
| 2015/0196250 A1 | 7/2015 | Nair |
| 2017/0323442 A1 | 11/2017 | Suehling |
| 2018/0010186 A1 | 1/2018 | Kullo |
| 2019/0019287 A1* | 1/2019 | Reda .................... G06V 10/764 |
| 2019/0087957 A1 | 3/2019 | Burris et al. |

OTHER PUBLICATIONS

PCT/US2020/027142, Oct. 21, 2021, International Preliminary Report on Patentability.
International Search Report and Written Opinion for International Application No. PCT/US2020/027142, mailed Jun. 23, 2020.
International Preliminary Report on Patentability for International Application No. PCT/US2020/027142, mailed Oct. 21, 2021.

* cited by examiner

| Category | Dice coefficient, % | Intersection over union, % | Absolute volume, mL | Volume % change |
|---|---|---|---|---|
| AAA | 91 ± 5 | 84 ± 9 | 45 ± 34 | 56 ± 3 |
| Endograft | 95 ± 3 | 90 ± 5 | 52 ± 67 | 47 ± 6 |
| AAA and endograft | 95 ± 2 | 91 ± 4 | 63 ± 55 | 53 ± 3 |

FIG. 17

METHOD AND APPARATUS FOR ANALYZING AORTIC ANEURYSMS AND ENDOLEAKS IN COMPUTED TOMOGRAPHY SCANS

CROSS-REFERENCE TO RELATED APPLICATIONS

This application is a national stage filing under 35 U.S.C. 371 of International Patent Application Serial No. PCT/US2020/027142, filed Apr. 8, 2020, and titled "METHOD AND APPARATUS FOR DETECTING ENDOLEAKS ON COMPUTERIZED TOMOGRAPHY SCANS AFTER ENDOVASCULAR AORTIC ANEURYSM REPAIR" which claims the benefit of priority under 35 U.S.C. § 119 (e) to U.S. Provisional Application Ser. No. 62/830,982, titled "METHOD AND APPARATUS FOR DETECTING ENDOLEAKS ON COMPUTERIZED TOMOGRAPHY SCANS AFTER ENDOVASCULAR AORTIC ANEURYSM REPAIR", filed on Apr. 8, 2019. the contents of each which are incorporated herein by reference in their entirety.

BACKGROUND

An abdominal aortic aneurysm (AAA) is an enlarged area in the lower part of the aorta. Abdominal aortic aneurysms can present a major surgical risk, and AAA rupture is the $15\text{-}19^{th}$ leading cause of death in the United States, ranking $10^{th}$ among men older than 55. Each year approximately 10,000 deaths are attributed to ruptured AAA with recognition that the estimate may be higher due to the silent nature of sudden death and infrequency of autopsies.

Surgical treatment for an AAA can involve open repair to replace the aneurysmal aorta with a graft or endovascular aneurysm repair (EVAR) to seal an aneurysm with a stent-graft. A risk associated with EVAR is the post-operative development of perigraft flow into the aortic aneurysm sac, a condition known as an endoleak.

SUMMARY

According to some embodiments, a method for diagnosing a patient having an abdominal aortic aneurysm (AAA) may be provided, the method comprising using at least one computer hardware processor to perform: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, a diagnosis of the patient, the diagnosis comprising information identifying at least one condition of the patient.

In some embodiments, classifying the property of the AAA may comprise predicting a location of the AAA in the input CTA images.

In some embodiments, classifying the property of the AAA may comprise predicting a presence or absence of an endoleak in the input CTA images.

In some embodiments, classifying the property of the AAA may comprise predicting a three-dimensional (3D) segmentation of the AAA in the input CTA images.

In some embodiments, classifying the property of the AAA may comprise predicting a three-dimensional (3D) segmentation of an endograft in the input CTA images.

In some embodiments, classifying the property of the AAA may comprise predicting a three-dimensional (3D) segmentation of an endoleak in the input CTA images.

In some embodiments, classifying the property of the AAA may comprise predicting a diameter of the AAA in the input CTA images.

In some embodiments, classifying the property of the AAA may comprise predicting a volume of the AAA in the input CTA images.

In some embodiments, classifying the property of the AAA may comprise predicting a volume of an endoleak in the input CTA images.

In some embodiments, classifying the property of the AAA may comprise predicting a severity of an endoleak in the input CTA images.

In some embodiments, the trained machine learning model may comprise a neural network model.

In some embodiments, the neural network model may include one or more convolutional layers.

In some embodiments, the neural network model may be trained using a training dataset comprising a set of training CTA images.

In some embodiments, the training CTA images may comprise postoperative CTA images.

In some embodiments, the training CTA images may comprise CTA images having multiple contrast phases.

In some embodiments, the neural network model may be trained using a dice loss function.

In some embodiments, the condition of the patient identified by the diagnosis may be an endoleak of the AAA.

In some embodiments, the diagnosis may identify a severity of the condition.

According to some embodiments, a system may be provided, the system comprising: at least one computer hardware processor; and at least one non-transitory computer-readable storage medium storing processor-executable instructions that, when executed by the computer hardware processor, cause the computer hardware processor to perform a method for diagnosing a patient having an abdominal aortic aneurysm (AAA), the method comprising: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, a diagnosis of the patient, the diagnosis comprising information identifying at least one condition of the patient.

According to some embodiments, at least one non-transitory computer-readable storage medium may be provided, storing processor-executable instructions that, when executed by a computer hardware processor, cause the computer hardware processor to perform a method for diagnosing a patient having an abdominal aortic aneurysm (AAA), the method comprising: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, a diagnosis of the patient, the diagnosis comprising information identifying at least one condition of the patient.

According to some embodiments, a method for determining a prognosis for a patient having an abdominal aortic aneurysm (AAA) may be provided, the method comprising using at least one computer hardware processor to perform: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, the prognosis of the patient, the prognosis comprising information indicating a predicted course of a condition of the patient.

In some embodiments, the condition of the patient may be a rupture of the AAA.

In some embodiments, the condition of the patient may be an endoleak of the AAA.

In some embodiments, the prognosis may include a predicted severity of the condition.

In some embodiments, the prognosis may include a predicted risk of rupture of the AAA.

In some embodiments, the prognosis may include a predicted growth rate of the AAA.

In some embodiments, classifying the property of the AAA may comprise predicting a presence or absence of an endoleak in the CTA images.

In some embodiments, classifying the property of the AAA may comprise predicting a three-dimensional (3D) segmentation of the AAA in the CTA images.

In some embodiments, classifying the property of the AAA may comprise predicting a three-dimensional (3D) segmentation of an endograft in the CTA images.

In some embodiments, classifying the property of the AAA may comprise predicting a three-dimensional (3D) segmentation of an endoleak in the input CTA images.

In some embodiments, classifying the property of the AAA may comprise predicting a diameter of the AAA in the CTA images.

In some embodiments, classifying the property of the AAA may comprise predicting a volume of the AAA in the CTA images.

In some embodiments, classifying the property of the AAA may comprise predicting a volume of an endoleak in the CTA images.

In some embodiments, the patient may have undergone an endovascular abdominal aortic aneurysm repair (EVAR) procedure, and the prognosis may be determined subsequent to the EVAR procedure.

In some embodiments, in the prognosis may be determined at least a year subsequent to the EVAR procedure.

According to some embodiments, a system may be provided, the system comprising: at least one computer hardware processor; and at least one non-transitory computer-readable storage medium storing processor-executable instructions that, when executed by the computer hardware processor, cause the computer hardware processor to perform a method for determining a prognosis for a patient having an abdominal aortic aneurysm (AAA), the method comprising: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, the prognosis of the patient, the prognosis comprising information indicating a predicted course of a condition of the patient.

According to some embodiments, at least one non-transitory computer-readable storage medium may be provided, storing processor-executable instructions that, when executed by a computer hardware processor, cause the computer hardware processor to perform a method for determining a prognosis for a patient having an abdominal aortic aneurysm (AAA), the method comprising: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, the prognosis of the patient, the prognosis comprising information indicating a predicted course of a condition of the patient.

According to some embodiments, a method for determining a treatment for a patient having an abdominal aortic aneurysm (AAA) may be provided, the method comprising using at least one computer hardware processor to perform: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, the treatment for the patient, the treatment comprising information indicating a clinical course of action to be taken in response to a condition of the patient.

In some embodiments, the condition of the patient may be a rupture of the AAA.

In some embodiments, the condition of the patient may be an endoleak of the AAA.

In some embodiments, the treatment may be based on a predicted severity of the condition.

In some embodiments, the treatment may be based on a predicted risk of rupture of the AAA.

In some embodiments, the treatment may be based on a predicted growth rate of the AAA.

In some embodiments, classifying the property of the AAA may comprise predicting a presence or absence of an endoleak in the CTA images.

In some embodiments, classifying the property of the AAA may comprise predicting a three-dimensional (3D) segmentation of the AAA in the CTA images.

In some embodiments, classifying the property of the AAA may comprise predicting a three-dimensional (3D) segmentation of an endograft in the CTA images.

In some embodiments, classifying the property of the AAA may comprise predicting a three-dimensional (3D) segmentation of an endoleak in the input CTA images.

In some embodiments, classifying the property of the AAA may comprise predicting a diameter of the AAA in the CTA images.

In some embodiments, classifying the property of the AAA may comprise predicting a volume of the AAA in the CTA images.

In some embodiments, classifying the property of the AAA may comprise predicting a volume of an endoleak in the CTA images.

In some embodiments, the clinical course of action indicated by the treatment may include a referral to a specialist.

In some embodiments, the clinical course of action indicated by the treatment may include a surgery.

In some embodiments, the surgery may be an endovascular abdominal aortic aneurysm repair procedure.

In some embodiments, the clinical course of action indicated by the treatment may include a course of drug dosages to be administered to the patient.

In some embodiments, the method may further comprise administering the treatment to the patient by taking the clinical course of action indicated by the treatment.

According to some embodiments, a system may be provided, the system comprising: at least one computer hardware processor; and at least one non-transitory computer-readable storage medium storing processor-executable instructions that, when executed by the computer hardware processor, cause the computer hardware processor to perform a method for determining a treatment for a patient having an abdominal aortic aneurysm (AAA), the method comprising: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, the treatment for the patient, the treatment comprising information indicating a clinical course of action to be taken in response to a condition of the patient.

According to some embodiments, at least one non-transitory computer-readable storage medium may be provided, storing processor-executable instructions that, when executed by a computer hardware processor, cause the computer hardware processor to perform a method for determining a treatment for a patient having an abdominal aortic aneurysm (AAA), the method comprising: accessing computed tomography angiography (CTA) images of a portion of the patient, the portion of the patient including the AAA of the patient; providing the CTA images as input to a trained machine learning model, the trained machine learning model being configured to classify a property of the AAA based on the CTA images; and determining, based on the classified property of the AAA, the treatment for the patient, the treatment comprising information indicating a clinical course of action to be taken in response to a condition of the patient.

According to some embodiments, a computer-implemented method may be provided for diagnosing an abdominal aortic aneurysm (AAA) in a patient, the method comprising using at least one computer hardware processor to perform: accessing abdominal computed tomography angiography (CTA) images of the patient; providing the abdominal CTA images as input to a trained machine learning model, the trained machine learning model being configured to determine a prediction related to the AAA in the abdominal CTA images; and determining, based on the prediction of the trained machine learning model, a diagnosis of the AAA in the patient.

In some embodiments, the prediction of the trained machine learning model may comprise a prediction of a presence or absence of the AAA in the abdominal CTA images.

In some embodiments, the prediction of the trained machine learning model may comprise a prediction of a location of the AAA.

In some embodiments, the prediction of the trained machine learning model may comprise a prediction of a bounding box around the AAA.

In some embodiments, the prediction of the trained machine learning model may comprise a prediction of a volume of the AAA.

According to some embodiments, a system may be provided, the system comprising: at least one computer hardware processor; and at least one non-transitory computer-readable storage medium storing processor-executable instructions that, when executed by the computer hardware processor, cause the computer hardware processor to perform a method for diagnosing an abdominal aortic aneurysm (AAA) in a patient, the method comprising: accessing abdominal computed tomography angiography (CTA) images of the patient; providing the abdominal CTA images as input to a trained machine learning model, the trained machine learning model being configured to determine a prediction related to the AAA in the abdominal CTA images; and determining, based on the prediction of the trained machine learning model, a diagnosis of the AAA in the patient.

According to some embodiments, at least one non-transitory computer-readable storage medium may be provided, storing processor-executable instructions that, when executed by a computer hardware processor, cause the computer hardware processor to perform a method for diagnosing an abdominal aortic aneurysm (AAA) in a patient, the method comprising: accessing abdominal computed tomography angiography (CTA) images of the patient; providing the abdominal CTA images as input to a trained machine learning model, the trained machine learning model being configured to determine a prediction related to the AAA in the abdominal CTA images; and determining, based on the prediction of the trained machine learning model, a diagnosis of the AAA in the patient.

According to some embodiments, a computer-implemented method may be provided for training a machine learning model to classify a property of an abdominal aortic aneurysm (AAA) in a patient, the method comprising using at least one computer hardware processor to perform: accessing a training dataset, the training dataset comprising a plurality of input computed tomography angiography (CTA) images, and a plurality of labels corresponding to the plurality of input CTA images and representing corresponding target outputs of the machine learning model, wherein the labels are related to the property of the AAA to be classified; and training the machine learning model to classify the property of the AAA, the training comprising repeatedly: providing a CTA image of the plurality of input CTA images as input to the machine learning model; determining, based on the provided CTA image, a prediction related to the property of the AAA to be classified; and based on the prediction and a label corresponding to the provided CTA image, updating the machine learning model.

In some embodiments, the CTA image may comprise multiple CTA image slices.

In some embodiments, training the machine learning model to classify the property of the AAA may comprise training a localization network of the machine learning model to predict a location of the AAA in the CTA image.

In some embodiments, predicting the location of the AAA in the CTA image may comprise predicting a bounding box around the AAA in the CTA image.

In some embodiments, the localization network may comprise a convolutional neural network.

In some embodiments, the localization network may include residual connections.

In some embodiments, training the machine learning model to classify the property of the AAA may comprise training an endoleak detection network to predict whether an endoleak is present in the CTA image.

In some embodiments, the endoleak detection network may comprise a convolutional neural network.

In some embodiments, the endoleak detection network may include residual connections.

In some embodiments, inputs to the endoleak detection network may be formed based on outputs of the localization network.

In some embodiments, predicting whether there is an endoleak present in the CTA image may comprise predicting whether there is an endoleak present in each CTA image slice of the multiple CTA image slices.

In some embodiments, training the machine learning model to classify the property of the AAA may comprise training a three-dimensional (3D) segmentation network to predict a 3D segmentation across the multiple CTA image slices of the CTA image.

In some embodiments, the 3D segmentation across the multiple CTA image slices may identify points occupied by the AAA, points occupied by an endograft, and points occupied by neither.

In some embodiments, the 3D segmentation across the multiple CTA image slices may identify points occupied by an endoleak.

In some embodiments, inputs to the 3D segmentation network may be formed based on outputs of the localization network.

In some embodiments, the 3D segmentation may be used to determine a volume of the AAA in the CTA image.

In some embodiments, the 3D segmentation may be used to determine a diameter of the AAA in the CTA image.

In some embodiments, the 3D segmentation may be used to determine a volume of an endoleak in the CTA image.

In some embodiments, accessing the training dataset may comprise generating the plurality of labels corresponding to the plurality of input CTA images.

In some embodiments, the plurality of labels may comprise: a first set of labels, corresponding to a first set of CTA images of the CTA input images, generated by one or more human beings; and a second set of labels, corresponding to a first set of CTA images of the CTA input images, generated based on predictions of the machine learning model.

In some embodiments, the machine learning model may be trained using the first set of CTA images and the first set of labels, prior to generating the second set of labels.

In some embodiments, the second set of labels may be reviewed by one or more human beings prior to training the machine learning model.

In some embodiments, a loss function of the machine learning model may be configured to separately account for the first set of labels and the second set of labels.

In some embodiments, the loss function of the machine learning model is a Dice loss function.

In some embodiments, the trained machine learning model may be stored on at least one non-transitory computer-readable storage medium.

According to some embodiments, a system may be provided, the system comprising: at least one computer hardware processor; and at least one non-transitory computer-readable storage medium storing processor-executable instructions that, when executed by the computer hardware processor, cause the computer hardware processor to perform a method for training a machine learning model to classify a property of an abdominal aortic aneurysm (AAA) in a patient, the method comprising: accessing a training dataset, the training dataset comprising a plurality of input computed tomography angiography (CTA) images, and a plurality of labels corresponding to the plurality of input CTA images and representing corresponding target outputs of the machine learning model, wherein the labels are related to the property of the AAA to be classified; and training the machine learning model to classify the property of the AAA, the training comprising repeatedly: providing a CTA image of the plurality of input CTA images as input to the machine learning model; determining, based on the provided CTA image, a prediction related to the property of the AAA to be classified; and based on the prediction and a label corresponding to the provided CTA image, updating the machine learning model.

According to some embodiments, at least one non-transitory computer-readable storage medium may be provided, storing processor-executable instructions that, when executed by a computer hardware processor, cause the computer hardware processor to perform a method for training a machine learning model to classify a property of an abdominal aortic aneurysm (AAA) in a patient, the method comprising: accessing a training dataset, the training dataset comprising a plurality of input computed tomography angiography (CTA) images, and a plurality of labels corresponding to the plurality of input CTA images and representing corresponding target outputs of the machine learning model, wherein the labels are related to the property of the AAA to be classified; and training the machine learning model to classify the property of the AAA, the training comprising repeatedly: providing a CTA image of the plurality of input CTA images as input to the machine learning model; determining, based on the provided CTA image, a prediction related to the property of the AAA to be classified; and based on the prediction and a label corresponding to the provided CTA image, updating the machine learning model.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 17 is a chart showing exemplary results of machine learning model(s) trained for predicting AAA/endograft 3D segmentations, in accordance with some embodiments of the technology described herein;

DETAILED DESCRIPTION

Figure 1:
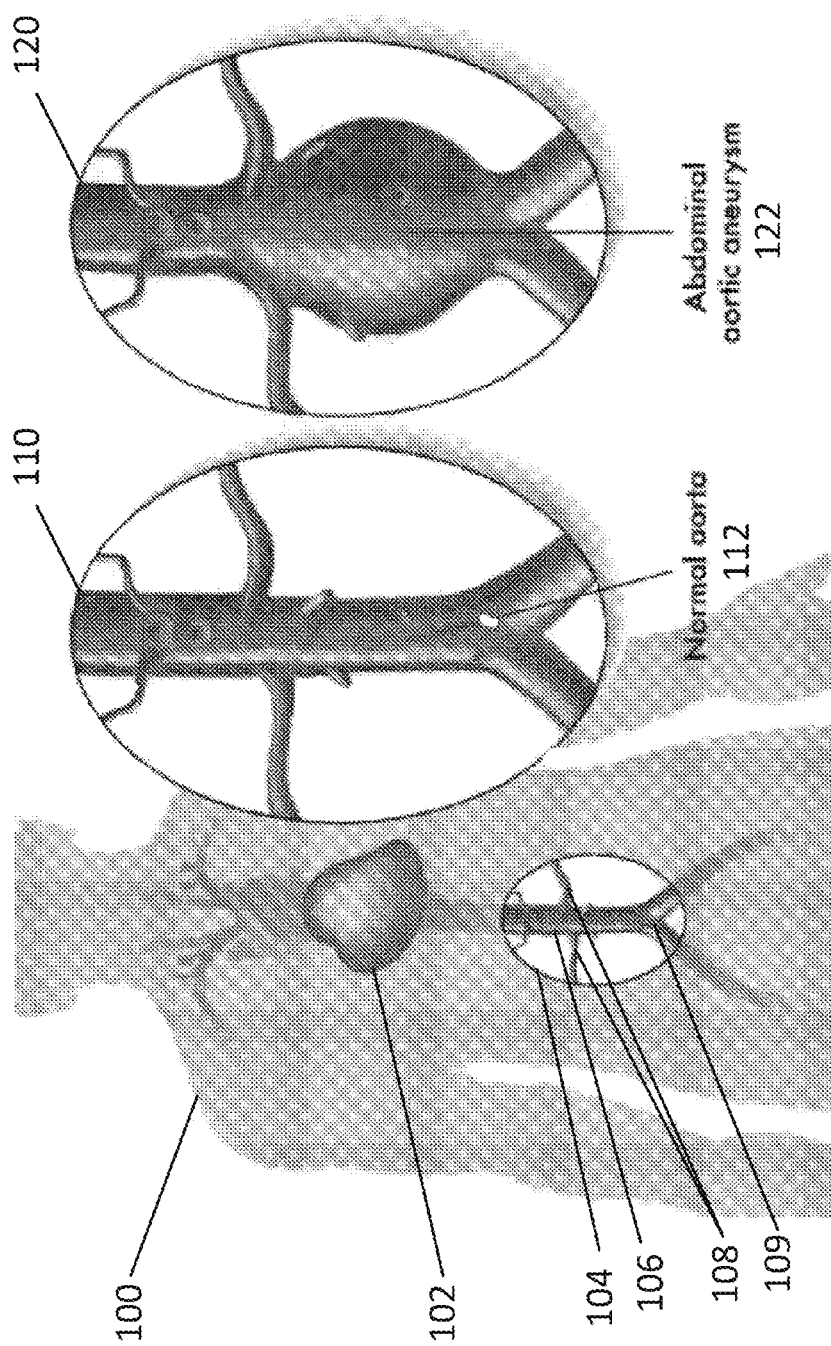
FIG. 1 illustrates a patient, a normal aorta, and an abdominal aortic aneurysm (AAA), in accordance with some embodiments of the technology described herein.

The inventors have developed and implemented machine learning techniques for predicting properties of abdominal aortic aneurysms (AAAs) and endoleaks in computed tomography angiography (CTA) images of human patients. The predicted properties may include the presence/absence of an AAA or endoleak, a location or segmentation of an AAA or endoleak, or a volume or diameter of an AAA or endoleak. In some embodiments, the predictions of the trained machine learning model may be used to determine a diagnosis, prognosis, or treatment for the patient.

In general, surgery is the treatment used to prevent life-threatening rupture once aneurysms such AAAs reach a critical diameter. Surgical treatment can involve open repair to replace the aneurysmal aorta with a graft, or endovascular repair to seal the aneurysm with a stent-graft. Approximately 45,000 abdominal aortic aneurysm repairs are performed annually in the U.S. with Endovascular AAA repair (EVAR) accounting for the majority (75%) of elective and an increasing amount of emergency AAA repairs for rupture.

Lifelong surveillance is generally required after EVAR to follow the development of the aneurysm and to detect endograft related complications, such as endoleaks, following the procedure. Post-operative surveillance may include imaging a patient with computerized tomography angiography (CTA). Three-phase computed tomography angiography (CTA) is a standard imaging modality for surveillance following an EVAR procedure, particularly for early imaging and surrounding re-interventions. The inventors have recognized and appreciated that endoleaks are a common consequence of EVAR procedures, occurring in up to 20% of EVAR patients, and have further recognized that an endoleak may be a prognostic marker for poor late outcomes for patients having an AAA, including aneurysm sac expansion, secondary interventions, and late rupture.

The inventors have recognized and appreciated that some properties relating to AAAs and endoleaks may not be tracked in the context of post-EVAR surveillance with CTA. For example, although there is emerging evidence that endoleak volume is a prognostic factor in AAA growth and rupture after repair, endoleak volume is not typically available to clinicians. The inventors have also recognized and appreciated that properties typically monitored during post-EVAR surveillance with CTA, including diagnosis of endoleaks and measurement of AAA volume, are frequently tracked with a lower accuracy and/or consistency than desired. In some cases, inconsistencies and/or inaccuracies in the monitored properties may be a consequence of inter-observer or intraobserver variability. In some cases, conventional techniques, such as for tracking diameter changes in the identification of AAA volume increase, have been challenged with reports of poor sensitivity.

Another challenge associated with the use computed tomography (CT) scans in the context of AAAs more generally (i.e., not limited to post-operative/EVAR contexts) is the failure to properly diagnose AAAs. This issue may arise, for example, because clinicians may not suspect AAA in patients of certain demographics. For example, diagnostic radiologists may not routinely assess for AAAs in women on CT scans of the abdomen because the prevalence of AAAs in adults over the age of 65 years is 3 to 4 times higher in men than women. In general, CT scans of the abdomen may be screened for AAA at a lower rate or with less accuracy than desired.

Consequently, the inventors have recognized and appreciated that there is a need for improved techniques for predicting properties of abdominal aortic aneurysms (AAAs) and endoleaks in computed tomography angiography (CTA) images. Accordingly, the inventors have developed techniques for using machine learning models to predict properties of AAAs and endoleaks based on CTA images, as well as techniques for training such machine learning models. As described herein, the predictions of such machine learning models may be used to determine improved diagnoses, prognoses, and treatments for patients, including patients who have already been diagnosed with an AAA, patients who have undergone EVAR surgery, and patients who have no prior AAA diagnosis. These techniques present a significant improvement of the prior art, as described herein at least with respect to FIGS. 16-18.

Accordingly, some embodiments of the technology described herein include a computer-implemented method for diagnosing an abdominal aortic aneurysm (AAA) in a patient. This method may involve using a computer hardware processor to perform: accessing (e.g., accessing from a non-transitory storage medium, such as a computer memory, or receiving via a network) abdominal computed tomography angiography (CTA) images of the patient; providing the abdominal CTA images (e.g., as an array of pixel of values, in a raw format, or having been pre-processed) as input to a trained machine learning model, the trained machine learning model being configured to determine a prediction related to the AAA in the abdominal CTA images; and determining, based on the prediction of the trained machine learning model, a diagnosis of the AAA in the patient (e.g., information identifying a presence/absence, size, location, volume, or diameter of the AAA). In some embodiments the machine learning model, as its output, may generate a prediction including: a prediction of a presence or absence of the AAA in the abdominal CTA images, a prediction of a location of the AAA, prediction of a bounding box around the AAA, or a prediction of a volume of the AAA.

Some embodiments of the technology described herein include a method for diagnosing a patient having an AAA (e.g., a patient who has been previously diagnosed with an AAA, who may or may not have undergone an EVAR procedure). The method may involve using a computer hardware processor to perform: accessing computed tomography angiography (CTA) images of a portion of the patient, the portion of the patient including the AAA of the patient (e.g., images from abdominal CTA scans, which may include multiple axial image slices); providing the CTA images as input to a trained machine learning model, the trained machine learning model being configured to classify a property of the AAA based on the CTA images; and determining, based on the classified property of the AAA, a diagnosis of the patient, the diagnosis comprising information identifying at least one condition (e.g., an endoleak, an AAA rupture) of the patient.

Some embodiments of the technology described herein include a method for determining a prognosis for a patient having an AAA (e.g., a patient who has been previously diagnosed with an AAA, who may or may not have undergone an EVAR procedure). The method may involve using a computer hardware processor to perform: accessing computed tomography angiography (CTA) images of a portion of the patient, the portion of the patient including the AAA of the patient (e.g., images from abdominal CTA scans, which may include multiple axial image slices); providing the CTA images as input to a trained machine learning model, the trained machine learning model being configured to classify a property of the AAA based on the CTA images; and determining, based on the classified property of the AAA, the prognosis of the patient, the prognosis comprising information indicating a predicted course of a condition (e.g., an endoleak, an AAA rupture) of the patient. The predicted course of the condition may include, for example, a predicted severity of the condition (e.g., measured via a numerical or qualitative scale, based on certain thresholds), a predicted risk of rupture of the AAA, a predicted growth rate of the AAA, or any combination thereof.

Some embodiments of the technology described herein include a method for determining a treatment for a patient having an AAA (e.g., a patient who has been previously diagnosed with an AAA, who may or may not have undergone an EVAR procedure). The method may involve using a computer hardware processor to perform: accessing computed tomography angiography (CTA) images of a portion of the patient, the portion of the patient including the AAA of the patient (e.g., images from abdominal CTA scans, which may include multiple axial image slices); providing the CTA images as input to a trained machine learning model, the trained machine learning model being configured to classify a property of the AAA based on the CTA images; and determining, based on the classified property of the AAA, the treatment for the patient, the treatment comprising information indicating a clinical course of action to be taken in response to a condition (e.g., an endoleak, an AAA rupture) of the patient. The clinical course of action may include, for example: a referral to a specialist, a surgery (such as EVAR), or a course of drug dosages to be administered to the patient.

In some embodiments the machine learning model, as its output, may generate a classification including: a location of the AAA in the input CTA images, a presence or absence of an endoleak in the input CTA images, a three-dimensional (3D) segmentation of the AAA in the input CTA images, a three-dimensional (3D) segmentation of an endograft in the input CTA images, a three-dimensional (3D) segmentation of an endoleak in the input CTA images, a diameter of the AAA in the input CTA images, a volume of the AAA in the input CTA images, a volume of an endoleak in the input CTA images, or a severity of an endoleak in the input CTA images.

Some embodiments of the technology described herein include a computer-implemented method for training a machine learning model (e.g., a neural network model, which may include multiple networks such as a convolutional neural network (CNN), Retina-Net, Res-Net, or 3D U-Net) to classify a property of an abdominal aortic aneurysm (AAA) in a patient. The method may involve using a computer hardware processor to perform: accessing a training dataset, the training dataset comprising a plurality of input computed tomography angiography (CTA) images, and a plurality of labels corresponding to the plurality of input CTA images (each of which may, for example, comprise multiple image slices) and representing corresponding target outputs of the machine learning model, wherein the labels are related to the property of the AAA to be classified (e.g., measurements of location, volume, or diameter of an AAA or endoleak, a 3D segmentation of an AAA and endograft, a type of an endoleak, or a 3D segmentation of an endoleak); and training the machine learning model to classify the property of the AAA, the training comprising repeatedly: providing a CTA image of the plurality of input CTA images as input to the machine learning model; determining, based on the provided CTA image, a prediction related to the property of the AAA to be classified; and based on the prediction and a label corresponding to the provided CTA image, updating the machine learning model (e.g., via a gradient descent, with a loss function).

In some embodiments, training the machine learning model to classify the property of the AAA may include training a localization network of the machine learning model to predict a location of the AAA in the CTA image. This may involve predicting a bounding box around the AAA in the CTA image. The localization network may comprise a convolutional neural network, and/or may include residual connections.

In some embodiments, training the machine learning model to classify the property of the AAA may comprise training an endoleak detection network to predict whether an endoleak is present in the CTA image. The endoleak detection network may comprise a convolutional neural network, and/or may include residual connections. The inputs to the endoleak detection network may be formed based on outputs of the localization network. In some embodiments, predicting whether there is an endoleak present in the CTA image may comprise predicting whether there is an endoleak present in each CTA image slice of multiple CTA image slices. In some embodiments, a type of the endoleak, as described herein at least with respect to FIG. 3, may be predicted.

In some embodiments, training the machine learning model to classify the property of the AAA may include training a three-dimensional (3D) segmentation network to predict a 3D segmentation across the multiple CTA image slices of the CTA image. The 3D segmentation across the multiple CTA image slices may identify points occupied by the AAA, points occupied by an endograft, and points occupied by neither. The 3D segmentation across the multiple CTA image slices may identify points occupied by an endoleak. The inputs to the 3D segmentation network may be formed based on outputs of the localization network. The 3D segmentation may be used to determine a volume of the AAA in the CTA image. The 3D segmentation may be used to determine a diameter of the AAA in the CTA image. The 3D segmentation may be used to determine a volume of an endoleak in the CTA image.

In some embodiments, accessing the training dataset may comprise generating the plurality of labels corresponding to the plurality of input CTA images. The plurality of labels may comprise: a first set of labels, corresponding to a first set of CTA images of the CTA input images, generated by one or more human beings; and a second set of labels, corresponding to a first set of CTA images of the CTA input images, generated based on predictions of the machine learning model. The machine learning model may be trained using the first set of CTA images and the first set of labels, prior to generating the second set of labels. The second set of labels may be reviewed by one or more human beings prior to training the machine learning model. The loss function of the machine learning model may be configured to separately account for the first set of labels and the second set of labels, and, in particular, may be a Dice loss function. In some embodiments, the trained machine learning model may be stored on at least one non-transitory computer-readable storage medium.

Following below are more detailed descriptions of various concepts related to, and embodiments of machine learning techniques for predicting properties of abdominal aortic aneurysms (AAAs) and endoleaks in computed tomography angiography (CTA) images. Various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1 illustrates an exemplary patient 100 to whom the techniques described herein may be applied, in accordance with some embodiments. The patient 100 may be a living human being, and need not be limited with respect to age, biological sex, or other characteristics. The patient 100 may or may not have an abdominal aortic aneurysm (AAA), may or may not have undergone a surgical procedure such as endovascular AAA repair (EVAR), and may or may not have been have been diagnosed with an AAA, endoleak, or any other condition.

The illustration of patient 100 includes a partial anatomical view of the patient's circulatory system, including the heart 102 and arteries of the patient. In the cut-out 104, the arteries of the abdomen of patient 100 are visible, presenting a view of the abdominal aorta 106, the renal arteries 108, and the aortic bifurcation 109. Two zoomed-in views of the anatomy of cut-out 104 are shown in cut-outs 110 and 120.

Cut-out 110 presents a view of normal abdominal aorta 112. As shown in the cut-out 110, the normal abdominal aorta may have a consistent aortic diameter, with no indication of an aneurysm.

Cut-out 120 presents a view of an abdominal aortic aneurysm (AAA) 122. Abdominal aortic aneurysms can occur at any of several locations along the abdominal aorta, including: suprarenal (above the renal arteries 108, at the level of the 11th rib); pararenal (immediately above/including the level of the renal arteries 108); juxtarenal (immediately below/including the level of the renal arteries 108); and infrarenal (below the renal arteries 108, at the aortic bifurcation 109). Although the illustrated AAA 122 is an infrarenal AAA, the techniques described herein may be applied to aneurysms occurring at any location along the abdominal aorta. In some cases, an AAA may be defined as an aortic diameter greater than 30 millimeters at any location along the abdominal aorta. In some cases, an AAA may be defined as a ratio of infrarenal to suprarenal aortic diameter greater than 1.5 times the normal infrarenal aortic diameter.

In general, the tendency of aortic aneurysms, such as AAA 122 in cut-out 120, is to expand over time. While year over year growth rates can vary between individuals, an average yearly growth rate may be between approximately 2-4 millimeters per year. The prognosis of patients with AAA may be related to a maximum diameter of the AAA, which can be correlated with the risk of rupture. In general, smaller AAAs between approximately 4-5.5 cm may be estimated to have an approximately 1% risk of rupture on an annual basis.

Depending on the prognosis of the AAA, surgery may be recommended to prevent life-threatening rupture. For example, surgery may be offered once an AAA reaches a threshold diameter. In some cases, the threshold to offer surgery to prevent rupture may vary slightly by biological sex. For example, guidelines may suggest that elective surgery be recommended for men with an aortic diameter over 5.5 cm, and for women with an aortic diameter over 5 cm in diameter. Surgical treatment for abdominal aortic aneurysms can involve open repair to replace the aneurysmal aorta with a graft or endovascular repair to seal the aneurysm with a stent-graft. Approximately 45,000 abdominal aortic aneurysm repairs are performed annually in the U.S. with Endovascular AAA repair (EVAR) accounting for the majority (75%) of elective and an increasing amount of emergency AAA repairs for rupture.

Figures 2A, 2B:
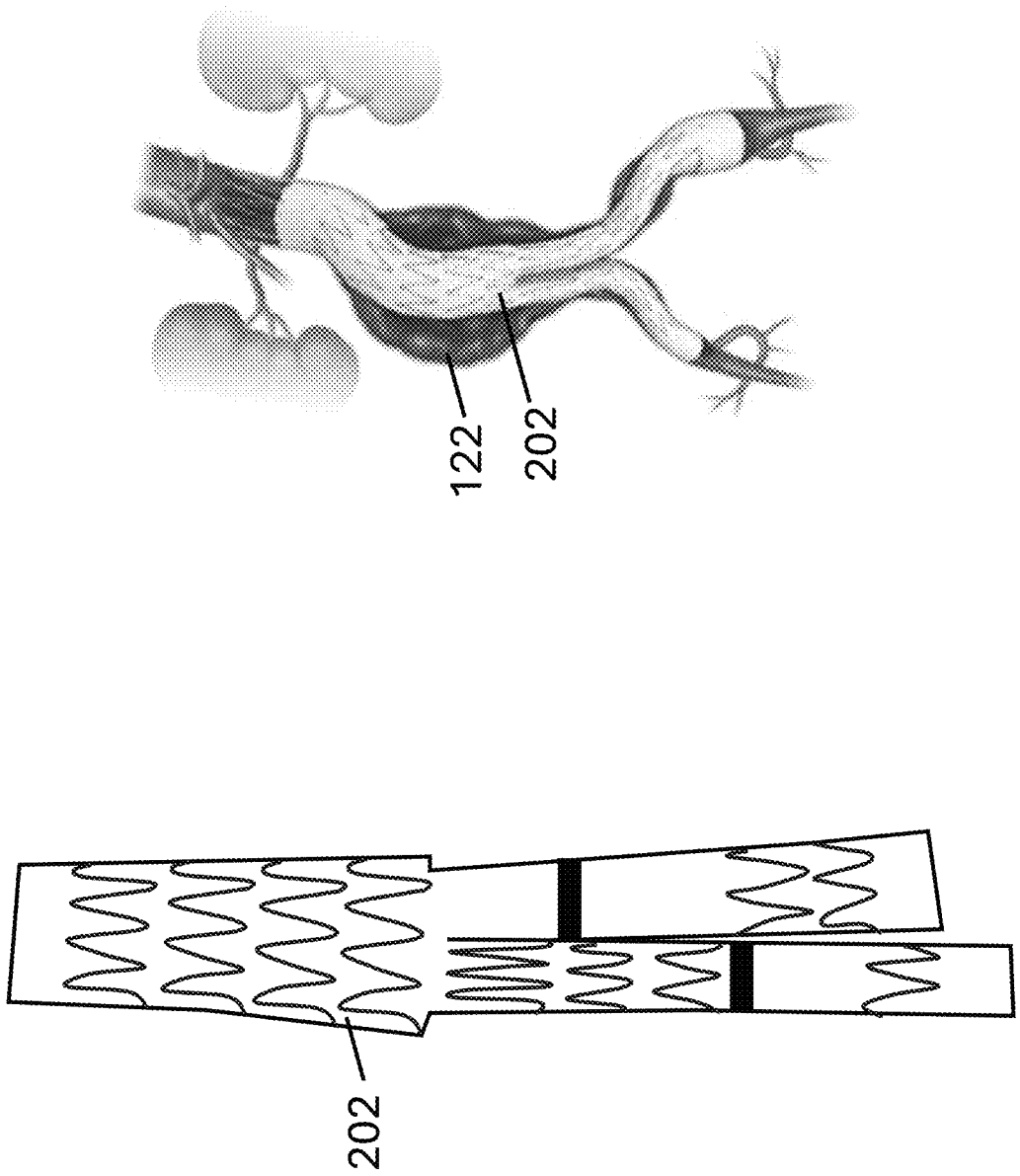
FIG. 2A illustrates an endograft, in accordance with some embodiments of the technology described herein.
FIG. 2B illustrates an endograft applied in the context of an endovascular AAA repair (EVAR) surgery, in accordance with some embodiments of the technology described herein.

FIG. 2A illustrates an endograft 202, and FIG. 2B illustrates the endograft 202 applied to an AAA 122 the context of an endovascular AAA repair (EVAR) surgery. The endograft 202 is an example of an iliac branch stent-graft, which may be surgically inserted in the abdominal aorta of a patient such that it extends approximately from between the renal arteries of the patient, down to either side of the aortic bifurcation. Other types of endografts, such as fenestrated or multi-branched stent-grafts are also possible, and may be applied with corresponding surgical techniques. Endoleaks, which involve perigraft flow into the residual aneurysm sac, can commonly arise following EVAR procedures, such as the one depicted in FIG. 2.

Figure 3:
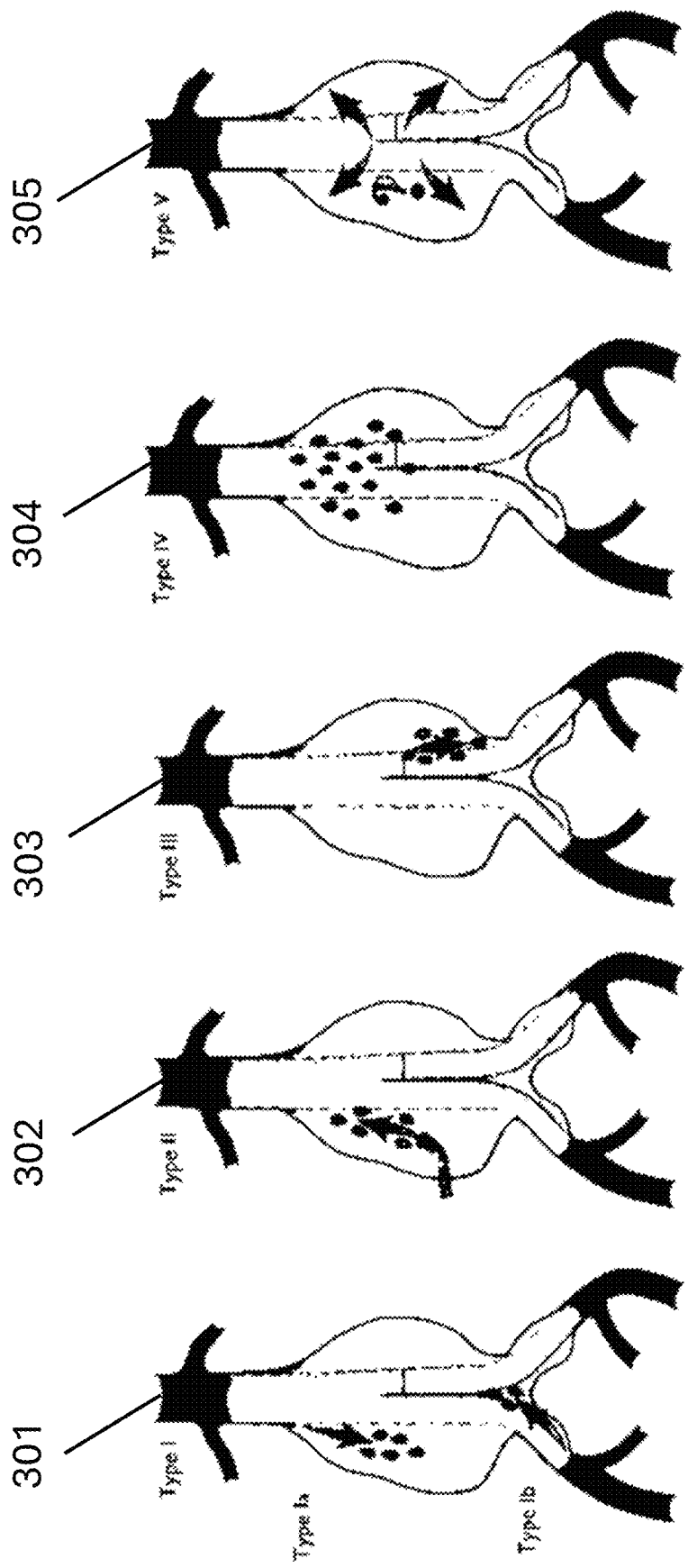
FIG. 3 is a diagram illustrating exemplary types of endoleaks that may arise, for example, following an EVAR surgery, in accordance with some embodiments of the technology described herein.

FIG. 3 is a diagram illustrating exemplary types of endoleaks that may arise, for example, following an EVAR surgery. Endoleak 301 is an example of a Type I endoleak, in which there is a failure to seal the artery above or below aneurysm sac, resulting in fluid flow into the aneurysm sac either at the top (Type Ia) or the bottom (Type Ib) of the sac.

Endoleak 302 is an example of a Type II endoleak, in which there is retrograde flow into the aneurysm sac from a branch vessel. Endoleak 303 is an example of a Type III endoleak, in which there is ineffective sealing of overlapping graft joints, or a fabric rupture, allowing fluid flow into the aneurysm sac. Endoleak 304 is an example of a Type IV endoleak, in which fluid flow into the aneurysm sac occurs due to the porosity of the endograft (i.e., flow through the material of the endograft, which may be, for example fabric). Endoleak 305 is an example of a Type V endoleak, in which aneurysm sac expansion occurs without clear evidence of endoleak origin.

Type II endoleaks can be the most common form of endoleaks, and may result from retrograde flow into the AAA from a branch vessel such as lumbar or inferior mesenteric arteries. Endoleaks may require secondary interventions which can be associated with some level of morbidity and cost, or can result in AAA rupture. Type II endoleaks may occur with a frequency of 10-30% after EVAR. Some Type II endoleaks have a benign trajectory while others are associated with AAA expansion and rupture. In general, with conventional techniques, the factors that cause Type II endoleaks to become clinically significant are not predicable.

Lifelong surveillance is generally required after EVAR to track the aneurysm and detect complications with the endograft. Surveillance may include clinical follow-up and imaging with computerized tomography angiography (CTA) and/or duplex ultrasound techniques. In some cases, three-phase (non-contrast, arterial, and delayed venous phase) CTA may be performed by technicians and interpreted by physicians as part of the surveillance. In general, imaging in the context of post-EVAR may be used to measure residual AAA sac diameter, evaluate for endoleak(s), and to detect other endograft related complications. Stabilized or decreasing AAA sac diameter may be correlated with long term success of treatment, while increasing diameter may be correlated with failed treatment and a poor overall prognosis.

Figure 4A:
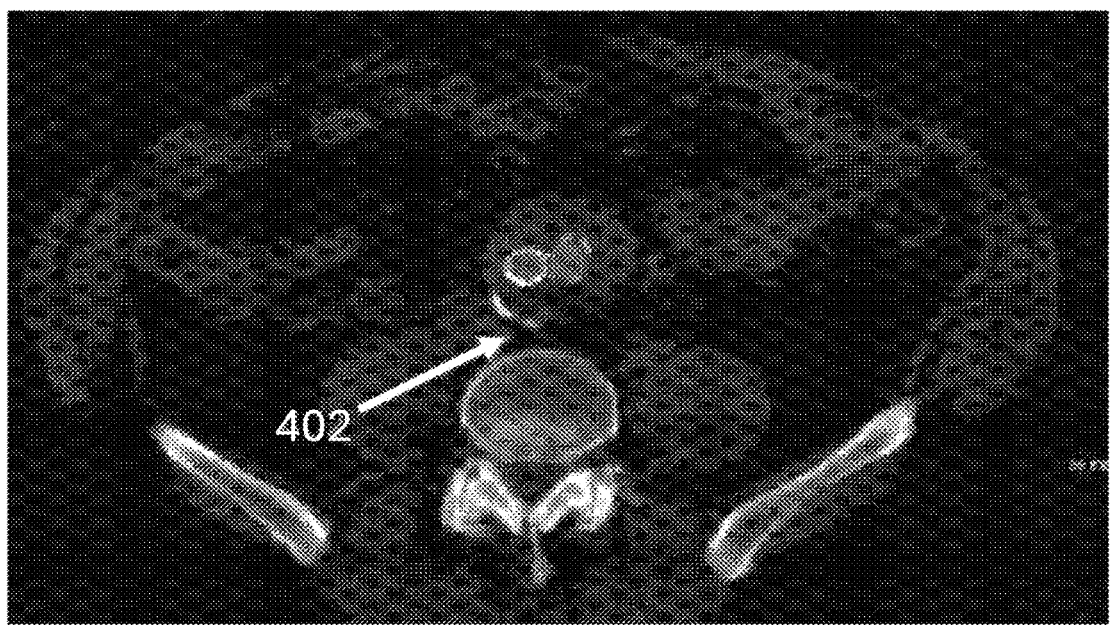
FIGS. 4A-B illustrate exemplary computed tomography angiography (CTA) scans including AAAs exhibiting endoleaks, in accordance with some embodiments of the technology described herein.
Figure 4B:
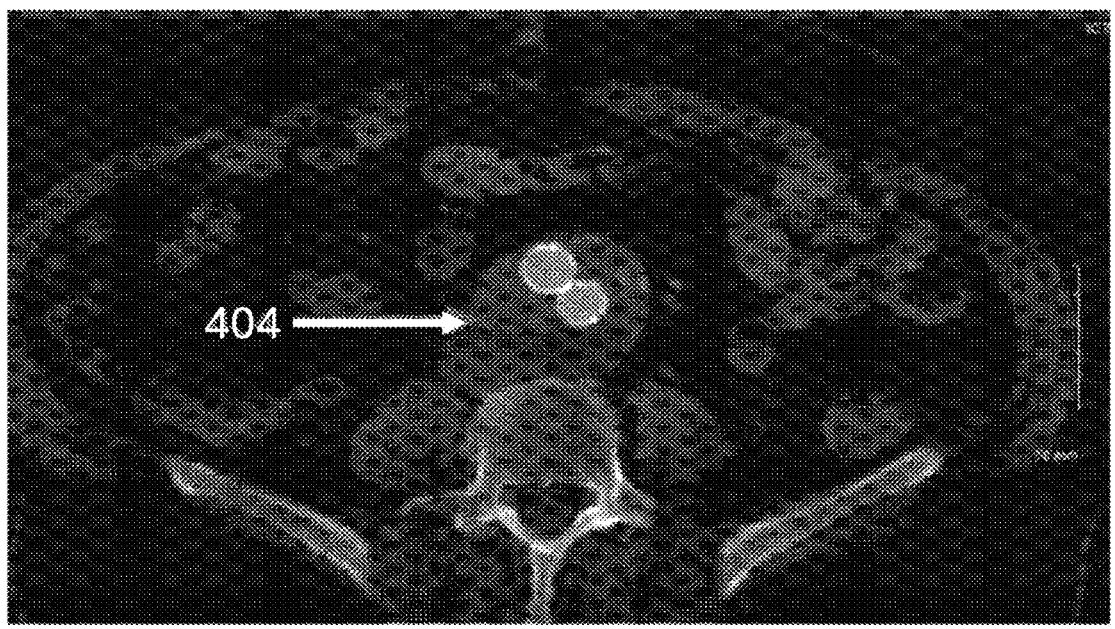

FIG. 4A and FIG. 4B illustrate exemplary computed tomography angiography (CTA) images including AAAs exhibiting endoleaks 402 and 404 respectively. The CTA images illustrated in FIGS. 4A-4B are axial slices of contrast phase CTA images. As discussed above, three-phase CTA involves the use of a contrast agent, such as iodinated contrast material, which may be injected or otherwise introduced into the patient's body, such that portions of the patient's anatomy that may otherwise be poorly captured or non-visible with CTA imaging will instead appear in the CTA image(s). The phases of three-phase CTA may include a non-contrast (or pre-contrast) phase, an arterial phase, and a delayed venous phase. Other multi-phase CTA modalities are also possible, and the techniques described herein are not limited in this respect. CTA scanning may be used to obtain CTA image slices in the axial, sagittal, or coronal anatomical planes.

Figure 5:
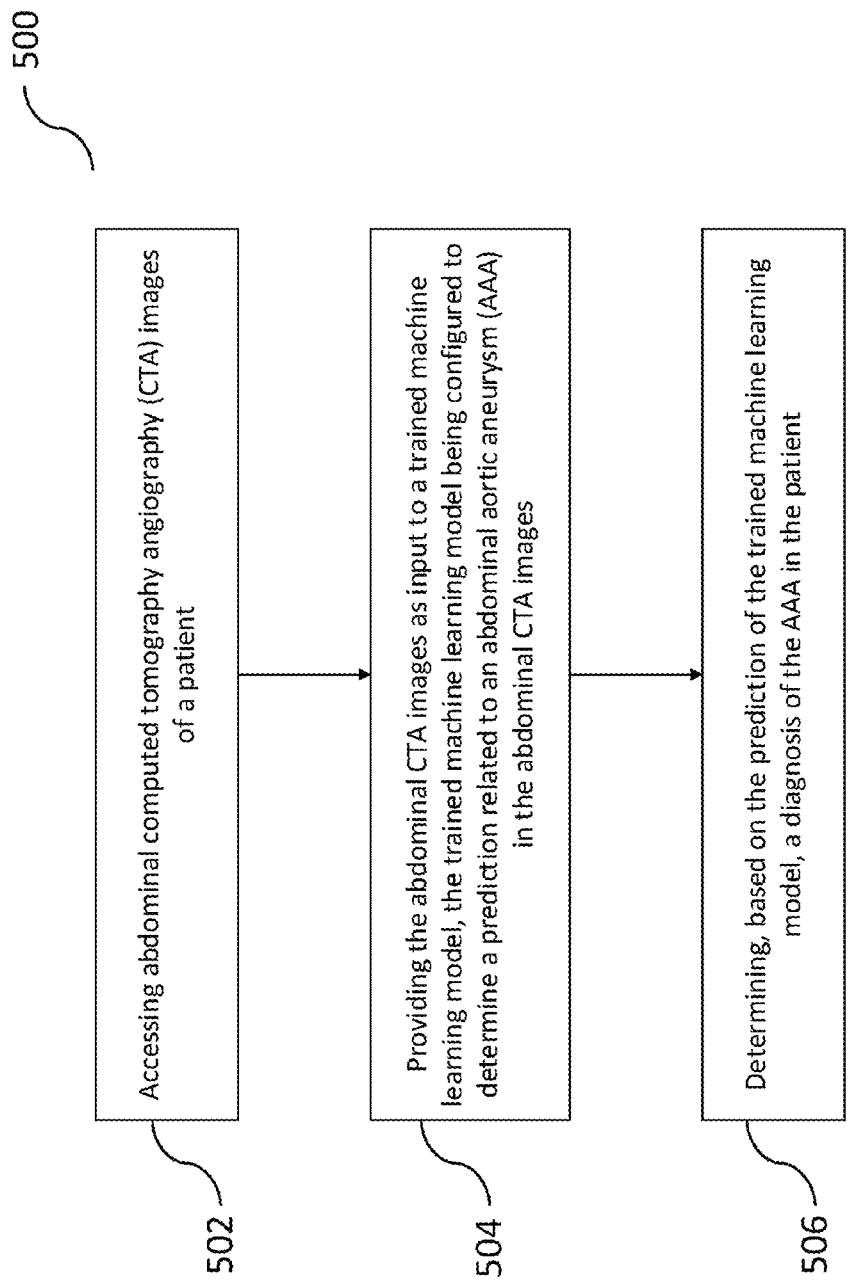
FIG. 5 is a flow diagram illustrating a method of diagnosing an AAA in a patient, in accordance with some embodiments of the technology described herein.

FIG. 5 is a flow diagram illustrating a method 500 of diagnosing an AAA in a patient. Steps of method 500 are carried out by one or more computer hardware processors. Method 500 may be used to screen for AAAs in abdominal CTA scans, potentially including scans collected for purposes other than AAA diagnosis. In general, method 500 can be applied to any abdominal CTA scan of any patient, regardless of indication of the CTA scan, to screen for AAA. The method 500 may thus allow a large quantity of CTA scans which would not normally be screened for AAA to be screened. For example, approximately 80 million CTA scans were obtained in the United States in 2015, of which a large percentage were abdominal CTA scans. If approximately a third of these CTA scans were of the abdomen, then method 500 could be applied to about 27 million CTA scans per year in the United States, to screen for AAA. Moreover, many clinicians do not suspect AAA in their female patients, and many diagnostic radiologists do not routinely assess for AAA in women on CTA scans of the abdomen, so method 500 could also help compensate for this oversight.

Method 500 begins at block 502 with accessing abdominal computed tomography angiography (CTA) images of a patient. The CTA images may include, for example, a set of consecutive axial CTA image slices that together make up one or more CTA scans of the patient. As discussed herein at least with respect to FIGS. 4A-B, the CTA images may include non-contrast, arterial, and delayed venous phase images. The CTA images may be accessed from a non-transitory storage medium, such as a computer memory, or may be received via a network connection (e.g., over the internet, having been stored on the cloud, et cetera). The CTA images may be stored in any appropriate format, such as arrays of pixel values, or in image file formats (such as JPEG, PNG, GIF, et cetera). The CTA images may be accessed simultaneously, or may be accessed in a number of batches over times.

Method 500 continues at block 504 with providing the abdominal CTA images as input to a trained machine learning model, the trained machine learning model being configured to determine a prediction related to an abdominal aortic aneurysm (AAA) in the abdominal CTA images. The machine learning model may be trained, for example, using the training techniques described herein at least with respect to FIGS. 9 and 12-15. In some embodiments, the prediction determined by the machine learning model at block 504 may be a binary classification indicating the presence or absence of an AAA in one or more of the CTA images. In some embodiments, the machine learning model may generate a prediction indicating the likelihood that an AAA is present in one or more of the CTA images (e.g., on a scale between 0 and 1, with 0 representing no AAA, and 1 representing an AAA). Additionally or alternatively, the machine learning model may generate a prediction regarding the location of an AAA in one or more of the CTA images. Such a prediction may include a prediction of a bounding box around the AAA (e.g., a rectangular area of a CTA image, or a three-dimensional rectangular prism volume over multiple CTA images, that is intended to bound the area and/or volume occupied by the AAA). In some embodiments, the machine learning model may generate a prediction regarding a three-dimensional (3D) segmentation of the AAA. The 3D segmentation of the AAA may comprise, for example, a set of pixels in the CTA images that the machine learning model predicts are occupied by the AAA (e.g., based on a predicted likelihood that each pixel is occupied by the AAA). The trained machine learning model may additionally or alternatively predict a volume of the AAA in the CTA images. This predicted volume may be based on a 3D segmentation of the AAA, for example, or it may be calculated directly from the CTA images. In some embodiments, the trained machine learning model may predict one or more diameters of the AAA (e.g., a maximum anterior-posterior diameters, a maximum diameter in the axial plane, two perpendicular diameters, an average diameter of two or more diameters, et cetera).

Method 500 continues at block 506 with determining, based on the prediction of the trained machine learning model, a diagnosis of the AAA in the patient. In some embodiments, the diagnosis may merely identify whether or not the patient has an AAA. In some embodiments, the diagnosis may identify a probability that the patient has an AAA. In some embodiments, the diagnosis may identify a location of an AAA (e.g., with a bounding box), or a volume or diameter of an AAA. In some embodiments the diagnosis may identify a severity of the AAA. In some embodiments, the diagnosis may be determined algorithmically from the prediction of the trained machine learning model, such as by a computer program executed by a processor. In some embodiments, the diagnosis may be made by a human being, such as a clinician, physician, radiologist, or other expert, based on the prediction of the trained machine learning model.

Figure 6:
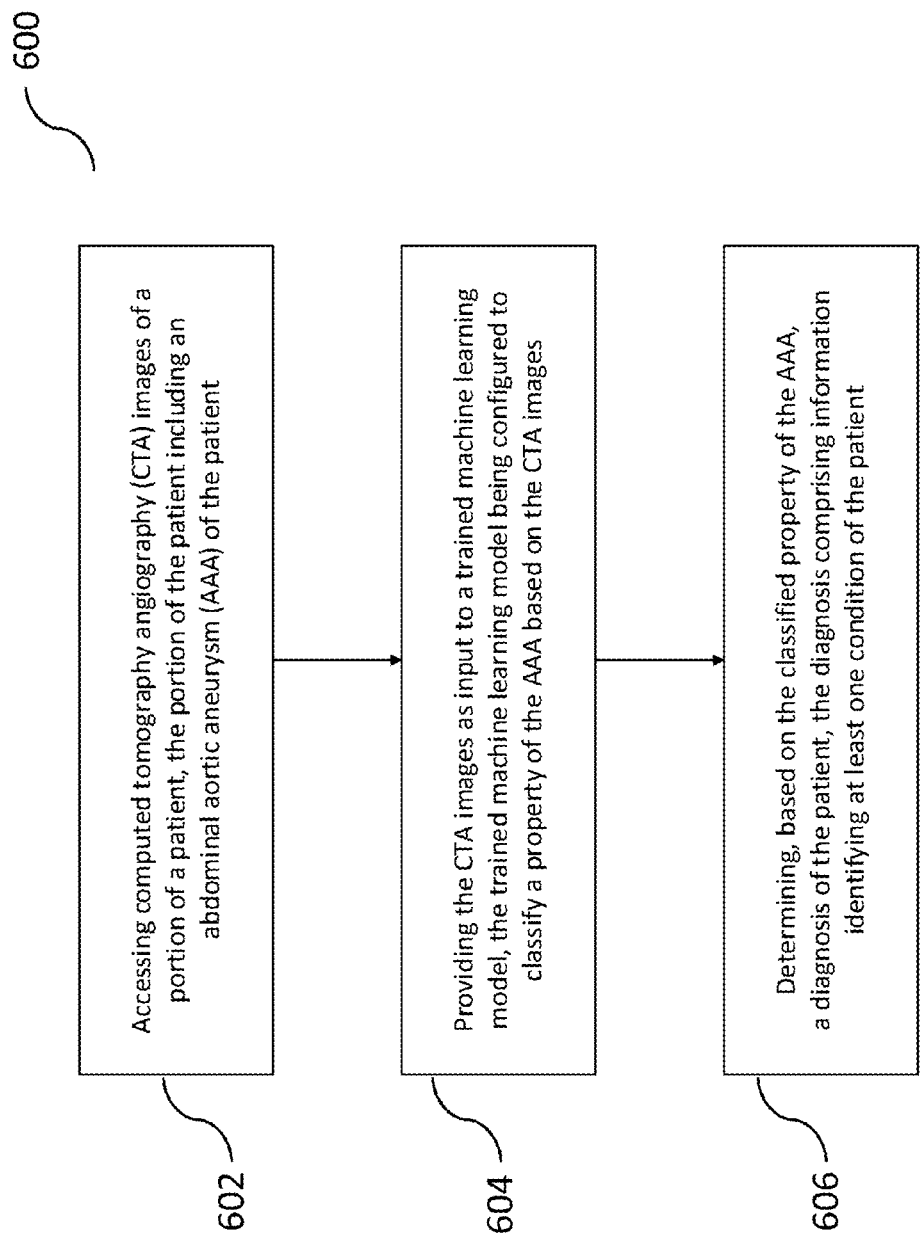
FIG. 6 is a flow diagram illustrating a method of diagnosing a patient having an AAA, in accordance with some embodiments of the technology described herein.

FIG. 6 is a flow diagram illustrating a method 600 of diagnosing a patient having an AAA. For example, method 600 may be applied to a patient having previously been diagnosed with an AAA. In some embodiments, the patient may have previously undergone an endovascular AAA repair (EVAR) procedure. Steps of method 600 are carried out by one or more computer hardware processors.

Method 600 begins at block 602 with accessing computed tomography angiography (CTA) images of a portion of a patient, the portion including an AAA of the patient. The CTA images may include, for example, a set of consecutive axial CTA image slices that together make up one or more CTA scans of the patient. As discussed herein at least with respect to FIGS. 4A-B, the CTA images may include non-contrast, arterial, and delayed venous phase images. The CTA images may be accessed from a non-transitory storage medium, such as a computer memory, or may be received via a network connection (e.g., over the internet, having been stored on the cloud, et cetera). The CTA images may be stored in any appropriate format, such as arrays of pixel values, or in image file formats (such as JPEG, PNG, GIF, et cetera). The CTA images may be accessed simultaneously, or may be accessed in a number of batches over times. In some embodiments, an endograft and/or an endoleak of the AAA, or other anatomical features of the abdomen of the patient, may also appear in one, some, or all of the CTA images. This is depicted, for example, in the CTA images of FIGS. 4A-B.

Method 600 continues at block 604 with providing the CTA images as input to a trained machine learning model, the trained machine learning model being configured to classify a property of the AAA based on the CTA images. The machine learning model may be trained, for example, using the training techniques described herein at least with respect to FIGS. 9 and 12-15. In some embodiments, classifying a property of the AAA at block 604 may include predicting a location of an AAA in one or more of the CTA images. This may include predicting a bounding box around the AAA (e.g., a rectangular area of a CTA image, or a three-dimensional rectangular prism volume over multiple CTA images, that is intended to bound the area and/or volume occupied by the AAA). Additionally or alternatively, the machine learning model at block 604 may determine a binary classification indicating the presence or absence of an endoleak in one or more of the CTA images. In some embodiments, the classification may indicate a likelihood that an endoleak is present in one or more of the CTA images (e.g., on a scale between 0 and 1, with 0 representing no endoleak, and 1 representing an endoleak). In some embodiments, the classification may indicate a predicted type of the endoleak (e.g., Type I, Type II, Type III, Type IV, or Type V).

In some embodiments, classifying a property of the AAA at block 604 may include predicting a three-dimensional (3D) segmentation of an AAA and an endograft of the AAA (e.g., an endograft inserted as part of an EVAR surgery) in the CTA images. The 3D segmentation of the AAA and endograft may comprise, for example, a set of pixels in the CTA images that the machine learning model predicts are occupied by the AAA, and a set of pixels in the CTA images that the machine learning model predicts are occupied by the endograft. The trained machine learning model may additionally or alternatively predict a volume of the AAA in the CTA images. This predicted volume may be based on a 3D segmentation of the AAA, for example, or it may be calculated directly from the CTA images. In some embodiments, the trained machine learning model may predict one or more diameters of the AAA (e.g., maximum anterior-posterior diameters, a maximum diameter in the axial plane, two perpendicular diameters, an average diameter of two or more diameters, et cetera). In some embodiments, classifying a property of the AAA at block 604 may include predicting a three-dimensional (3D) segmentation of an endoleak in the CTA images. This may include, for example, identifying pixels that the machine learning model predicts are occupied by an endoleak. In some embodiments, a volume of the endoleak in the CTA images may be predicted as part of classifying a property of the AAA at block 604.

Method 600 continues at block 606 with determining, based on the classified property of the AAA, a diagnosis of the patient, the diagnosis comprising information identifying at least one condition of the patient. In some embodiments, the condition may be an endoleak, and the diagnosis may merely identify whether or not the patient has an endoleak. In some embodiments, the diagnosis may identify a probability that the patient has an endoleak. In some embodiments, the diagnosis may identify a location of an AAA (e.g., with a bounding box), or a volume or diameter of an AAA. In some embodiments the diagnosis may identify a severity of the AAA or an endoleak of the AAA. In some embodiments, the diagnosis may be determined algorithmically from the classified property of the AAA, such as by a computer program executed by a processor. In some embodiments, the diagnosis may be made by a human being, such as a clinician, physician, radiologist, or other expert, based on the classification of the trained machine learning model.

Figure 7:
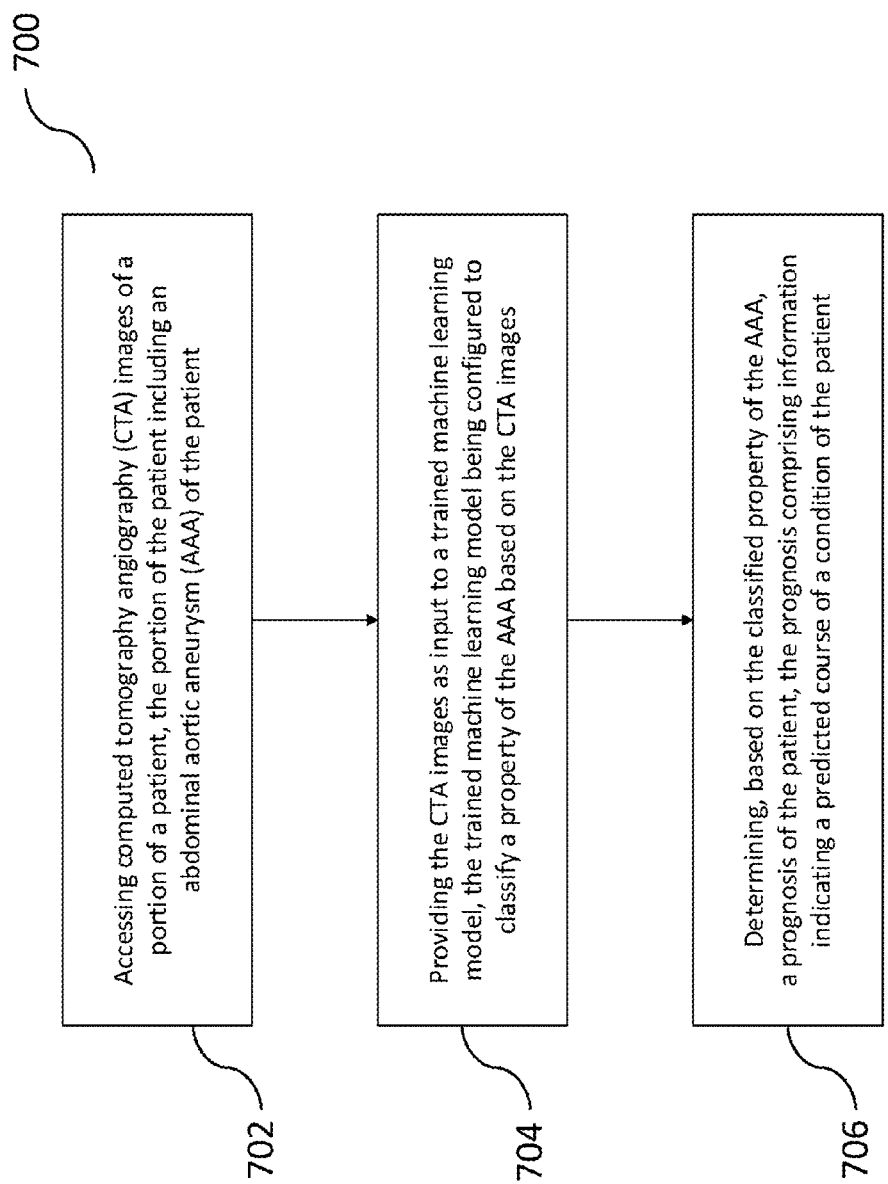
FIG. 7 is a flow diagram illustrating a method of determining a prognosis for a patient having an AAA, in accordance with some embodiments of the technology described herein.

FIG. 7 is a flow diagram illustrating a method 700 of determining a prognosis for a patient having an AAA. For example, method 700 may be applied to a patient having previously been diagnosed with an AAA. In some embodiments, the patient may have previously undergone an endovascular AAA repair (EVAR) procedure. Steps of method 700 are carried out by one or more computer hardware processors.

Method 700 begins at block 702 with accessing computed tomography angiography (CTA) images of a portion of a patient, the portion including an AAA of the patient. The CTA images may include, for example, a set of consecutive axial CTA image slices that together make up one or more CTA scans of the patient. As discussed herein at least with respect to FIGS. 4A-B, the CTA images may include non-contrast, arterial, and delayed venous phase images. The CTA images may be accessed from a non-transitory storage medium, such as a computer memory, or may be received via a network connection (e.g., over the internet, having been stored on the cloud, et cetera). The CTA images may be stored in any appropriate format, such as arrays of pixel values, or in image file formats (such as JPEG, PNG, GIF, et cetera). The CTA images may be accessed simultaneously, or may be accessed in a number of batches over times. In some embodiments, an endograft and/or an endoleak of the AAA, or other anatomical features of the abdomen of the patient, may also appear in one, some, or all of the CTA images. This is depicted, for example, in the CTA images of FIGS. 4A-B.

Method 700 continues at block 704 with providing the CTA images as input to a trained machine learning model, the trained machine learning model being configured to classify a property of the AAA based on the CTA images. The machine learning model may be trained, for example, using the training techniques described herein at least with respect to FIGS. 9 and 12-15. In some embodiments, classifying a property of the AAA at block 704 may include predicting a location of an AAA in one or more of the CTA images. This may include predicting a bounding box around the AAA (e.g., a rectangular area of a CTA image, or a three-dimensional rectangular prism volume over multiple CTA images, that is intended to bound the area and/or volume occupied by the AAA). Additionally or alternatively, the machine learning model at block 704 may determine a binary classification indicating the presence or absence of an endoleak in one or more of the CTA images. In some embodiments, the classification may indicate a likelihood that an endoleak is present in one or more of the CTA images (e.g., on a scale between 0 and 1, with 0 representing no endoleak, and 1 representing an endoleak). In some embodiments, the classification may indicate a predicted type of the endoleak (e.g., Type I, Type II, Type III, Type IV, or Type V).

In some embodiments, classifying a property of the AAA at block 704 may include predicting a three-dimensional (3D) segmentation of an AAA and an endograft of the AAA (e.g., an endograft inserted as part of an EVAR surgery) in the CTA images. The 3D segmentation of the AAA and endograft may comprise, for example, a set of pixels in the CTA images that the machine learning model predicts are occupied by the AAA, and a set of pixels in the CTA images that the machine learning model predicts are occupied by the endograft. The trained machine learning model may additionally or alternatively predict a volume of the AAA in the CTA images. This predicted volume may be based on a 3D segmentation of the AAA, for example, or it may be calculated directly from the CTA images. In some embodiments, the trained machine learning model may predict one or more diameters of the AAA (e.g., maximum anterior-posterior diameters, a maximum diameter in the axial plane, two perpendicular diameters, an average diameter of two or more diameters, et cetera). In some embodiments, classifying a property of the AAA at block 704 may include predicting a three-dimensional (3D) segmentation of an endoleak in the CTA images. This may include, for example, identifying pixels that the machine learning model predicts are occupied by an endoleak. In some embodiments, a volume of the endoleak in the CTA images may be predicted as part of classifying a property of the AAA at block 704.

Method 700 continues at block 706 with determining, based on the classified property of the AAA, a prognosis of the patient, the prognosis comprising information indicating a predicted course of a condition of the patient. In some embodiments, the condition may be an endoleak. In some embodiments, the condition may be a rupture of a the AAA. In some embodiments the prognosis may identify a severity of the condition (e.g., the AAA or an endoleak of the AAA), or a predicted risk of the condition worsening (e.g., a predicted risk of rupture of the AAA, a predicted growth rate of the AAA, a predicted trajectory or type of endoleak, et cetera). In some embodiments, the prognosis may be determined algorithmically from the classified property of the AAA, such as by a computer program executed by a processor. In some embodiments, the prognosis may be made by a human being, such as a clinician, physician, radiologist, or other expert, based on the classification of the trained machine learning model.

Figure 8:
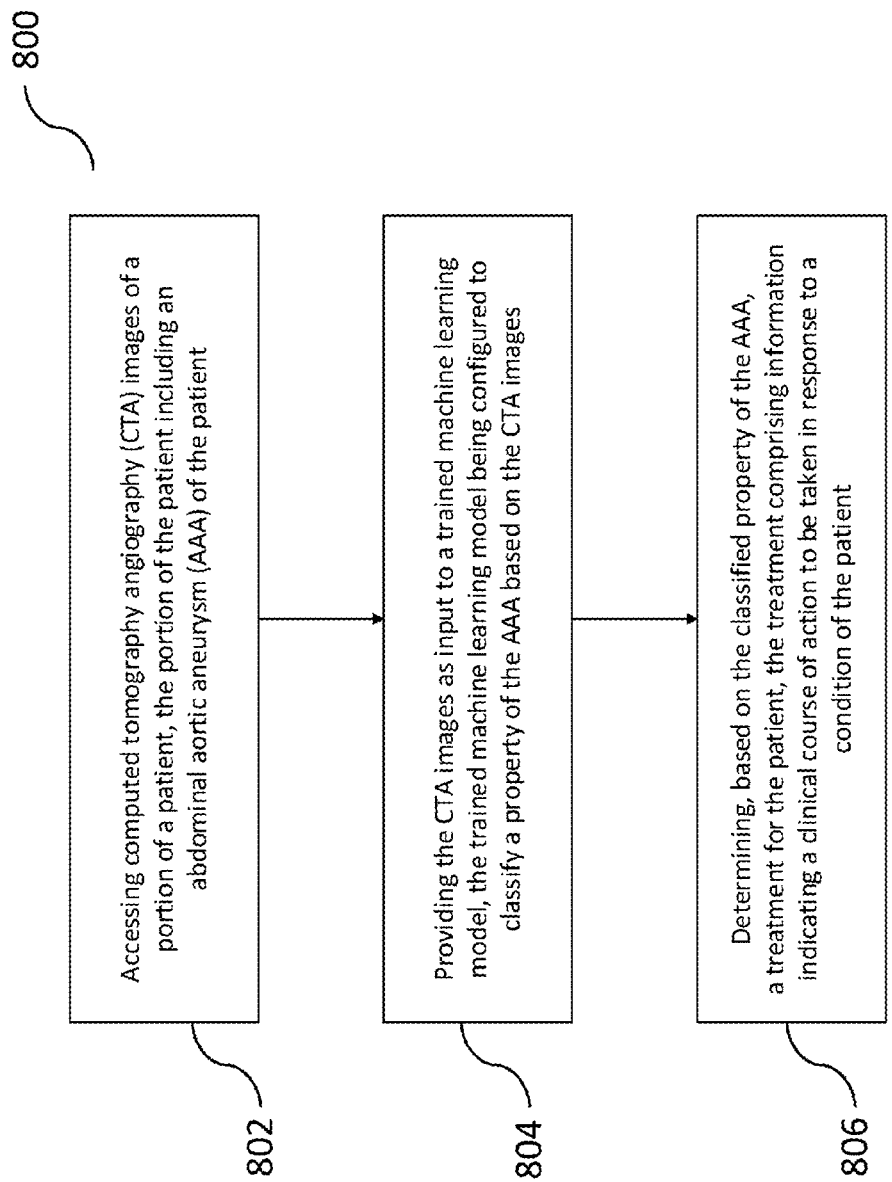
FIG. 8 is a flow diagram illustrating a method of determining a treatment for a patient having an AAA, in accordance with some embodiments of the technology described herein.

FIG. 8 is a flow diagram illustrating a method 800 of determining a treatment for a patient having an AAA. For example, method 800 may be applied to a patient having previously been diagnosed with an AAA. In some embodiments, the patient may have previously undergone an endovascular AAA repair (EVAR) procedure. Steps of method 800 are carried out by one or more computer hardware processors.

Method 800 begins at block 802 with accessing computed tomography angiography (CTA) images of a portion of a patient, the portion including an AAA of the patient. The CTA images may include, for example, a set of consecutive axial CTA image slices that together make up one or more CTA scans of the patient. As discussed herein at least with respect to FIGS. 4A-B, the CTA images may include non-contrast, arterial, and delayed venous phase images. The CTA images may be accessed from a non-transitory storage medium, such as a computer memory, or may be received via a network connection (e.g., over the internet, having been stored on the cloud, et cetera). The CTA images may be stored in any appropriate format, such as arrays of pixel values, or in image file formats (such as JPEG, PNG, GIF, et cetera). The CTA images may be accessed simultaneously, or may be accessed in a number of batches over times. In some embodiments, an endograft and/or an endoleak of the AAA, or other anatomical features of the abdomen of the patient, may also appear in one, some, or all of the CTA images. This is depicted, for example, in the CTA images of FIGS. 4A-B.

Method 800 continues at block 804 with providing the CTA images as input to a trained machine learning model, the trained machine learning model being configured to classify a property of the AAA based on the CTA images. The machine learning model may be trained, for example, using the training techniques described herein at least with respect to FIGS. 9 and 12-15. In some embodiments, classifying a property of the AAA at block 804 may include predicting a location of an AAA in one or more of the CTA images. This may include predicting a bounding box around the AAA (e.g., a rectangular area of a CTA image, or a three-dimensional rectangular prism volume over multiple CTA images, that is intended to bound the area and/or volume occupied by the AAA). Additionally or alternatively, the machine learning model at block 804 may determine a binary classification indicating the presence or absence of an endoleak in one or more of the CTA images. In some embodiments, the classification may indicate a likelihood that an endoleak is present in one or more of the CTA images (e.g., on a scale between 0 and 1, with 0 representing no endoleak, and 1 representing an endoleak). In some embodiments, the classification may indicate a predicted type of the endoleak (e.g., Type I, Type II, Type III, Type IV, or Type V).

In some embodiments, classifying a property of the AAA at block 804 may include predicting a three-dimensional (3D) segmentation of an AAA and an endograft of the AAA (e.g., an endograft inserted as part of an EVAR surgery) in the CTA images. The 3D segmentation of the AAA and endograft may comprise, for example, a set of pixels in the CTA images that the machine learning model predicts are occupied by the AAA, and a set of pixels in the CTA images that the machine learning model predicts are occupied by the endograft. The trained machine learning model may additionally or alternatively predict a volume of the AAA in the CTA images. This predicted volume may be based on a 3D segmentation of the AAA, for example, or it may be calculated directly from the CTA images. In some embodiments, the trained machine learning model may predict one or more diameters of the AAA (e.g., maximum anterior-posterior diameters, a maximum diameter in the axial plane, two perpendicular diameters, an average diameter of two or more diameters, et cetera). In some embodiments, classifying a property of the AAA at block 804 may include predicting a three-dimensional (3D) segmentation of an endoleak in the CTA images. This may include, for example, identifying pixels that the machine learning model predicts are occupied by an endoleak. In some embodiments, a volume of the endoleak in the CTA images may be predicted as part of classifying a property of the AAA at block 804.

Method 800 continues at block 806 with determining, based on the classified property of the AAA, a treatment for the patient, the treatment comprising information indicating a clinical course of action to be taken in response to a condition of the patient. In some embodiments, the condition may be an endoleak. In some embodiments, the condition may be a rupture of a the AAA. In some embodiments the treatment may be based on a severity of the condition (e.g., the AAA or an endoleak of the AAA), or a predicted risk of the condition worsening (e.g., a predicted risk of rupture of the AAA, a predicted growth rate of the AAA, a predicted trajectory or type of endoleak, et cetera). In some embodiments, the clinical course of action indicated by the treatment may include a referral to specialist (e.g., a specialist in aneurysms of the abdominal aorta). In some embodiments, the clinical course of action indicated by the treatment may include a surgery, such as endovascular abdominal aortic aneurysm repair (EVAR). In some embodiments, the clinical course of action indicated by the treatment includes a course of drug dosages to be administered to the patient. In some embodiments, the treatment may be determined algorithmically from the classified property of the AAA, such as by a computer program executed by a processor. In some embodiments, the treatment may be determined by a human being, such as a clinician, physician, radiologist, or other expert, based on the classification of the trained machine learning model. In some embodiments, method 800 may further comprise administering the treatment determined at block 806.

Figure 9:
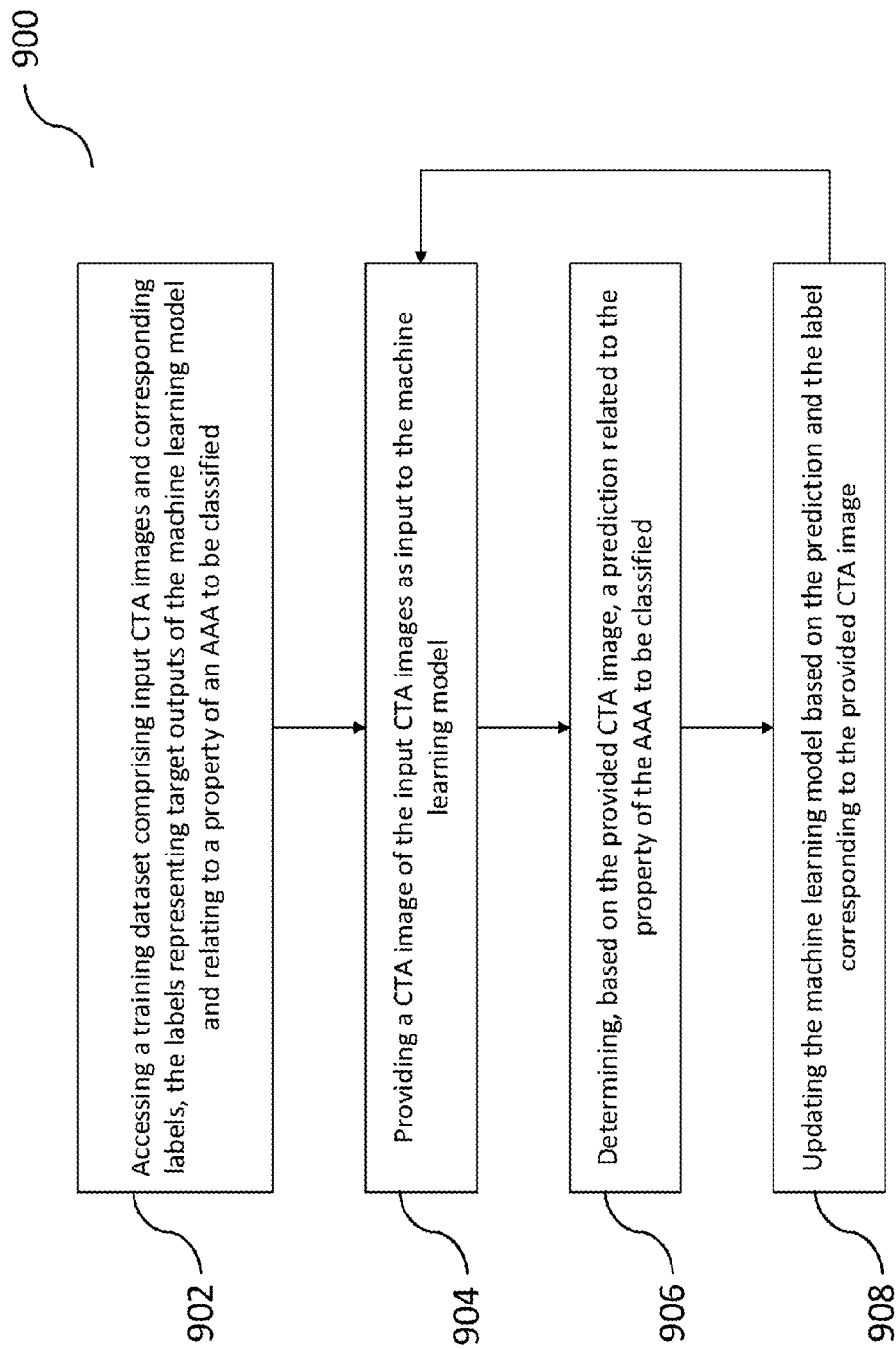
FIG. 9 is a flow diagram illustrating a method of training a machine learning model to classify a property of an AAA in a patient, in accordance with some embodiments of the technology described herein.

FIG. 9 is a flow diagram illustrating a method 900 of training a machine learning model to classify a property of an AAA in a patient. Steps of method 900 are carried out by one or more computer hardware processors. An exemplary implementation of the method 900 is described herein at least with respect to FIGS. 12-15.

Method 900 begins at block 902 with accessing a training dataset comprising input CTA images and corresponding labels, the labels representing target outputs of the machine learning model and relating to a property of an AAA to be classified. The input CTA images may be abdominal CTA images obtained from one or more CTA scans of human patients, and, in some embodiments, multiple CTA images may be obtained from one or more CTA scans of the same patient. The CTA images may include, for example, a set of consecutive axial CTA image slices that together make up the one or more CTA scans of one or more patients. As discussed herein at least with respect to FIGS. 4A-B, the CTA images may include non-contrast, arterial, and delayed venous phase images. In some embodiments, the input CTA images may include only CTA images of select phase(s), for example, only arterial and delayed venous phase CTA images (i.e., not including non-contrast phase CTA images). The CTA images may be accessed from a non-transitory storage medium, such as a computer memory, or may be received via a network connection (e.g., over the internet, having been stored on the cloud, et cetera). The CTA images may be stored in any appropriate format, such as arrays of pixel values, or in image file formats (such as JPEG, PNG, GIF, et cetera). The CTA images may be accessed simultaneously, or may be accessed in a number of batches over times. In some embodiments, an endograft and/or an endoleak of the AAA, or other anatomical features of the abdomen of a patient, may also appear in one, some, or all of the CTA images. This is depicted, for example, in the CTA images of FIGS. 4A-B.

The labels corresponding to the input CTA images represent target outputs of the machine learning model. For example, the labels may indicate a location of an AAA in one or more of the CTA images, such as with a bounding box around the AAA (e.g., a rectangular area of a CTA image, or a three-dimensional rectangular prism volume over multiple CTA images, that is intended to bound the area and/or volume occupied by the AAA). Additionally or alternatively, the labels may include a binary classification indicating the presence or absence of an endoleak in one, some, or all of the CTA images. In some embodiments, the label may indicate a likelihood that an endoleak is present in one or more of the CTA images (e.g., on a scale between 0 and 1, with 0 representing no endoleak, and 1 representing an endoleak). In some embodiments, the labels may indicate a predicted type of the endoleak (e.g., Type I, Type II, Type III, Type IV, or Type V)

In some embodiments, the labels may include a three-dimensional (3D) segmentation of an AAA and an endograft of the AAA (e.g., an endograft inserted as part of an EVAR surgery) in the CTA images. The 3D segmentation of the AAA and endograft may comprise, for example, a set of pixels in the CTA images that are occupied by the AAA, and a set of pixels in the CTA images that are occupied by the endograft. The labels may additionally or alternatively include a volume of the AAA in the CTA images, or one or more diameters of the AAA in the CTA images (e.g., maximum anterior-posterior diameters, a maximum diameter in the axial plane, two perpendicular diameters, an average diameter of two or more diameters, et cetera). In some embodiments, the labels may include a three-dimensional (3D) segmentation of an endoleak in the CTA images. The 3D segmentation of the endoleak may include, for example, a set of pixels in the CTA images that are occupied by the endoleak. In some embodiments, the labels may include a volume of an endoleak in the CTA images.

The labels corresponding to the input CTA images may be accessed from a non-transitory storage medium, such as a computer memory, or they may be received via a network connection (e.g., over the internet, having been stored on the cloud, et cetera). In some embodiments, accessing the labels may include creating the labels. For example, in some cases, the input CTA images may be manually labelled (e.g., an expert such as a physician or radiologist may label the CTA images by specifying whether an AAA or endoleak is present, by drawing a bounding box around an AAA, by selecting pixels representing AAA, endograft, or endoleak, or indicating a label in any other suitable manner). In some cases, the labels may be created automatically with partial or no supervision. For example, in some embodiments, labels may be extracted from radiology reports associated with the CTA images (e.g., a radiology report may note the presence of an AAA or endoleak in a CTA scan, and/or may note a range of CTA image slices in which the AAA or endoleak appears). In some embodiments, the labels may be predicted by the machine learning model, as described herein at least with respect to FIG. 12. Regardless of how the labels are created, the labels may be further reviewed by an expert and/or manually corrected.

The method 900 continues at block 904 with providing a CTA image of the input CTA images as input to the machine learning model. The CTA image may be provided as input to the machine learning model as part of a batch of CTA images, as described herein at least with respect to FIGS. 12-15.

The method 900 continues at block 906 with determining, based on the provided CTA image(s), a prediction related to the property of the AAA to be classified. As described herein at least with respect to FIGS. 12-15, the machine learning model may determine the prediction related to the property of the AAA to be classified by passing the CTA image(s) through multiple neural networks comprising the machine learning model, as well as performing pre and/or post-processing steps.

The method 900 continues at block 908 with updating the machine learning model based on the prediction and the label(s) corresponding to the provided CTA image(s). This may include computing a loss function based on the prediction and label, where the loss function may result in a value representing a degree of difference between the label and the prediction. In some cases, the loss function may be a cross-entropy loss function, a Dice loss function, or any other suitable loss function. Updating the machine learning model may comprise updating a set of weights or multiple sets of weights comprising the machine learning model. This may be done, for example, with a back-propagation process.

As indicated by the arrow leading from block 908 to block 904 in FIG. 9, in some embodiments, the actions of blocks 904, 906, and 908 may be repeated, forming a training loop. This training loop may serve to train the machine learning model by repeatedly updating it, resulting in a trained machine learning model. Note that the updating performed at block 908 need not happen in the same manner with each repetition. For example, a learning rate hyperparameter for the model may be set such that the extent to which the machine learning model is updated with each repetition decreases or otherwise varies over time. The number of times that the training loop is repeated as part of method 900 may be determined, for example, by the quantity of training data (i.e., the CTA images and corresponding labels), and/or may be determined based on when the machine learning model is considered trained (e.g., when an average loss drops below a threshold, or any suitable metric representing the success of the machine learning model reaches a desired value).

Figure 10:
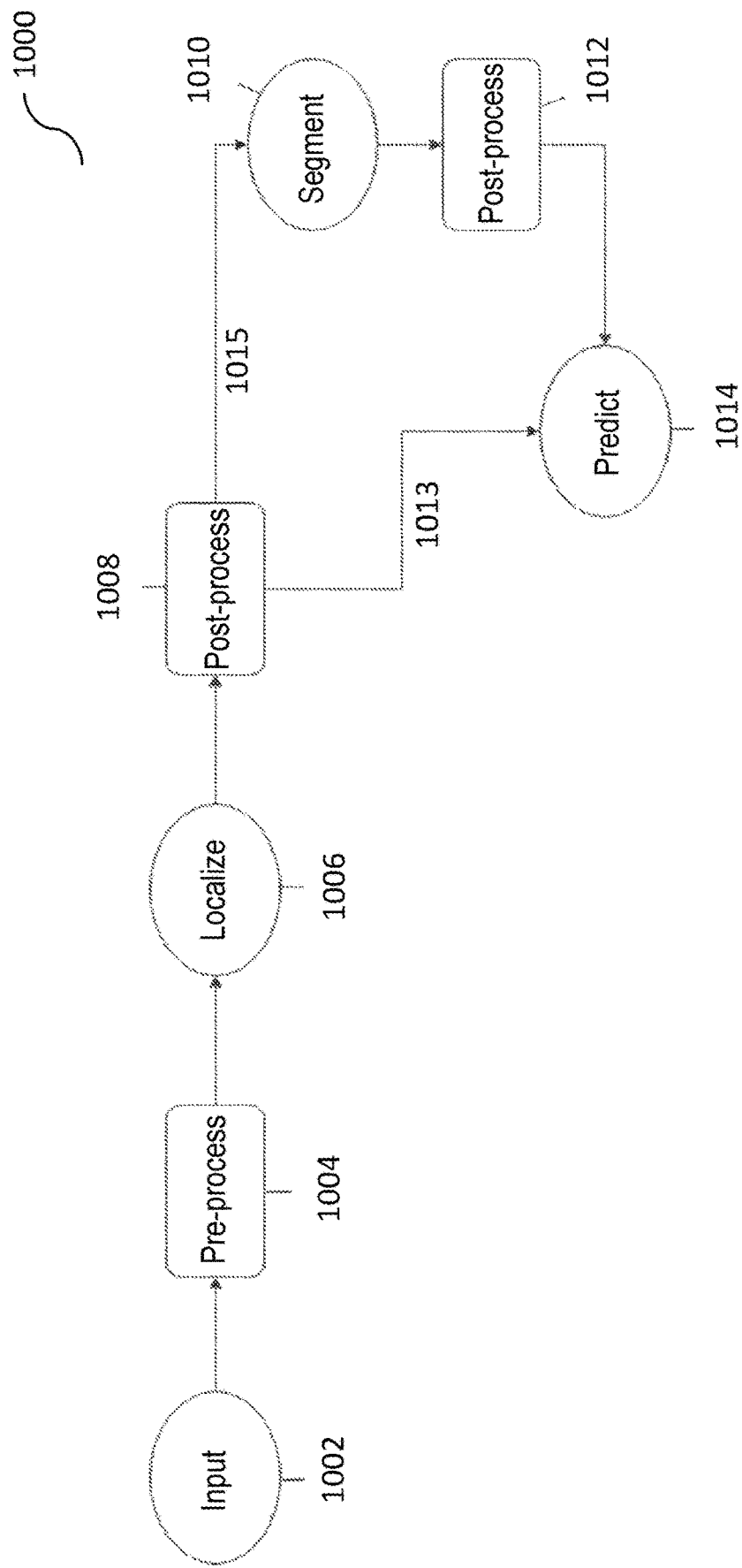
FIG. 10 is a flow diagram illustrating a method of using a machine learning model to generate predictions relating to one or more properties of an AAA, in accordance with some embodiments of the technology described herein.
Figure 11:
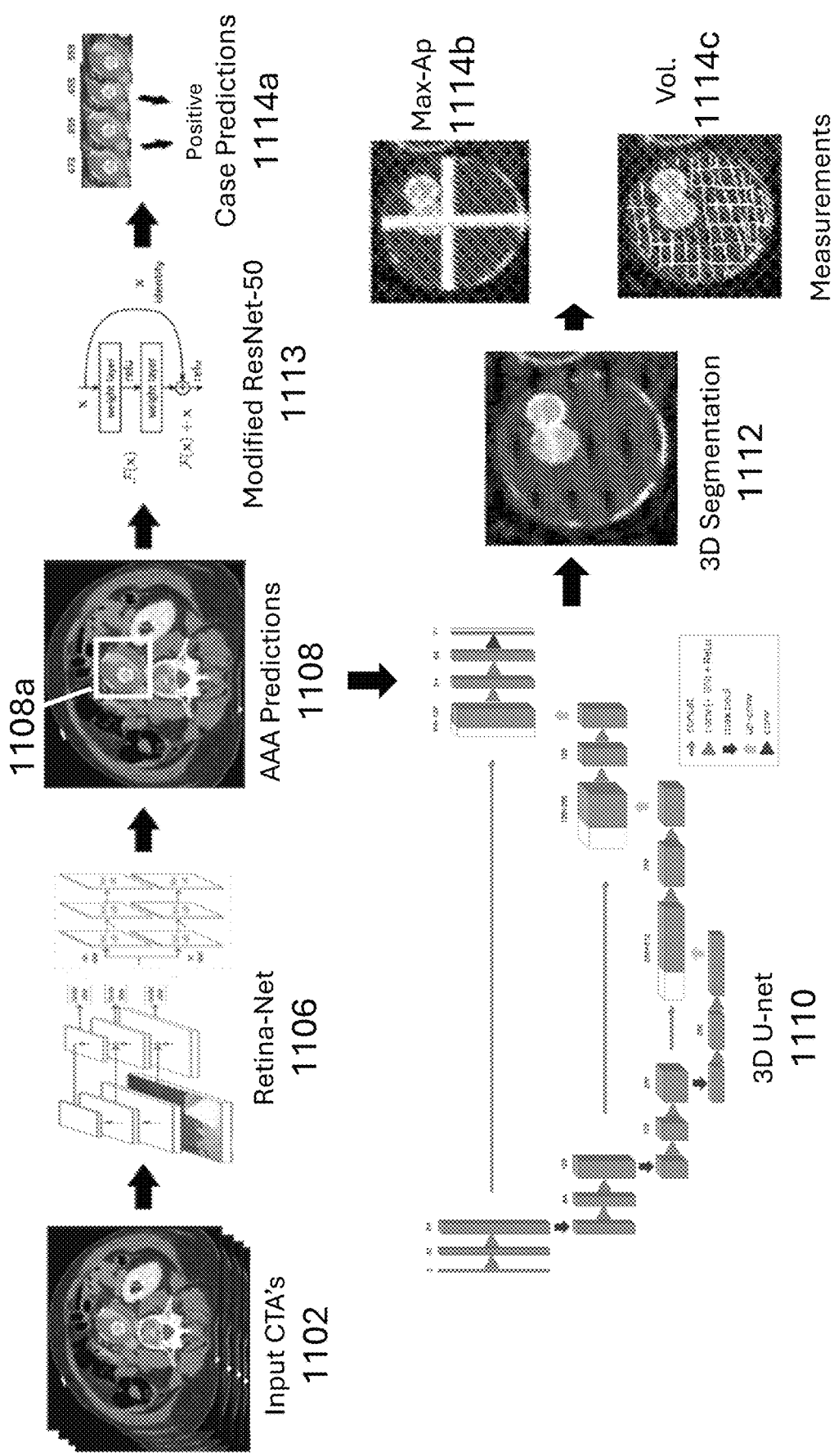
FIG. 11 is a flow diagram illustrating an exemplary implementation of the method of FIG. 10, in accordance with some embodiments of the technology described herein.

FIG. 10 is a flow diagram illustrating a method 1000 of using a machine learning model to generate predictions relating to one or more properties of an AAA, and FIG. 11 is a flow diagram illustrating an exemplary implementation of method 1000 of FIG. 10. Steps of method 1000 are carried out by one or more computer hardware processors.

At block 1002 in FIG. 10, the input(s) for the machine learning model are accessed or received. As discussed herein at least with respect to FIGS. 5-8, the input(s) may be CT or CTA images stored in any suitable format, such as a digitized format, and the input(s) may be accessed and/or received in any suitable manner. The input(s) are illustrated in FIG. 11 at block 1102, which shows multiple CTA images, such as may be obtained from one or more abdominal CTA scans of a patient. The CTA images may comprise multiple CTA image slices, which may be, for example, consecutive axial slices.

At block 1004 in FIG. 10, the input(s) are pre-processed. This may include normalizing the pixel values in the input(s) (e.g., to be values on a scale from 0 to 1, or any other suitable scale), cropping and/or padding the input(s) such that they are of a desired size (e.g., 512 by 512 pixels), or any other appropriate pre-processing techniques.

At block 1006 in FIG. 10, an area of interest is localized within the input(s). In particular, the area of interest may contain an AAA, endograft, endoleak, and/or other features of the abdomen of the patient of relevance to the techniques described herein. The area of interest may be indicated with a bounding box. In FIG. 11, block 1106 illustrates that localization may be performed, for example, with a neural network trained to predict the location of the relevant features. Particularly, block 1106 shows that a Retina-Net neural network may be used to perform the localization and identify, for example, a bounding box around an area occupied by an AAA in the input(s). Details of an exemplary implementation of such a neural network are described herein, at least with respect to FIG. 13 below.

At block 1008 in FIG. 10, the results of the localization are post-processed. In some embodiments, this may involve transforming the results of the localization (e.g., the areas of the input(s) indicated by the bounding boxes) into a desired size or format, or performing any other suitable post-processing. For example, the results of localization may be cropped, padded, scaled, up-sampled, or down-sampled so as to result in post-processed images of a desired size or format. In some embodiments, the post-processed images may be 128×128 images, stored, for example, in 128×128 arrays. In some embodiments, the post-processing may also involve determining, from the localization results, a three-dimensional (3D) bounding box containing localized areas across multiple images. For example, the post-processing may transform the localization results into a 128×128×128 array, representing a corresponding 128×128×128 volume containing the localized areas across all of the multiple images. Exemplary results of post-processing are shown in FIG. 11 at block 1108. In this example, the bounding box 1108a contains an area occupied by an AAA, as well and an endograft and endoleak, in the input CTA images.

The flow of method 1000 splits into two paths, path 1013 and path 1015, following block 1008. Either or both of these paths may be followed as part of method 1000, and the steps of either path may be performed consecutively, simultaneously, staggered with one another, or in any other suitable manner.

As shown in FIG. 10, path 1013 leads to block 1014, where a prediction is generated regarding a property of an AAA in the input(s), based on the post-processed results from block 1008. In this case, following path 1013, the prediction generated may be a binary classification of the property. For example, the binary classification may indicate whether an AAA is present in the input(s) (e.g., based on a degree of confidence in a bounding box around the AAA). In some embodiments, the binary classification may indicate whether an endoleak of the AAA is present in the input(s). In this case, as shown in FIG. 11 at block 1113, generating the prediction may include using a neural network to generate the prediction. In the example of FIG. 11, the neural network at block 1113 generates a prediction for each image slice of the input(s), indicating whether an endoleak is predicted to be present in that image slice (e.g., on a scale from 0 to 1, with 0 representing no endoleak and 1 representing an endoleak). The neural network of block 1113 may be, for example, a modified Res-Net 50, as described herein at least with respect to FIG. 14. At block 1114*a*, which corresponds to block 1014 in FIG. 10, an overall prediction regarding the presence of an endoleak in the input(s) is generated. The overall prediction may be based on the individual image slice predictions, and may comprise an overall binary classification (e.g., a 0 or 1 representing whether an endoleak is present in the input(s)), an overall likelihood that an endoleak is present (e.g., on a scale from 0 to 1), or an identification of image slices having an endoleak (e.g., image slices with a binary classification indicating the presences of an endoleak, or with a likelihood of having an endoleak over a threshold).

In FIG. 10, path 1015 leads to block 1010, where a three-dimensional (3D) segmentation of the input(s) is generated based on the post-processed results from block 1008. In particular, the 3D segmentation may be performed on the volume defined by a 3D bounding box determined at block 1008. Generating the 3D segmentation may comprise determining, for each voxel within the volume, a prediction regarding whether that voxel is occupied by an endograft, an AAA, or neither. Generating the 3D segmentation may comprise determining, for each voxel within the volume, a prediction regarding whether that voxel is occupied by an endoleak, or not occupied by an endoleak. As shown in FIG. 11 at block 1110, the 3D segmentation of block 1010 may be generated by a neural network. In the illustrated example, the neural network may be a 3D U-Net, as described herein at least with respect to FIG. 15.

At block 1012, the results of the 3D segmentation from block 1010 are post-processed. In some embodiments, post-processing at block 1012 may include removing outliers from the predicted 3D segmentation. This may involve identifying clusters of voxels having the same classification (e.g., indicating the presence of an AAA, endograft, or endoleak), and manipulating these clusters so as to remove outliers. In some embodiments, this may include changing the classification of some voxels. The post-processing may also include generating a mask for each of the classes segmented at block 1010 (e.g., a mask indicating the voxels occupied by an AAA, a mask indicating the voxels occupied by an endograft, and/or a mask indicating the voxels occupied by an endoleak). The mask may be a binary mask, have the same voxel dimensions as the 3D bounding box of block 1008 (e.g., a 128×128×128 volume containing 0s and 1s indicating whether an AAA is present, a 128×128×128 volume containing 0s and 1s indicating whether an endograft is present, and/or a 128×128×128 volume containing 0s and 1s indicating whether an endoleak is present).

At block 1014 in FIG. 10, a prediction is generated regarding a property of an AAA in the input(s). In this case, having taken path 1015, the prediction at block 1014 may be based on the post-processed 3D segmentation(s) from block 1012. In some embodiments, the prediction may include a predicted volume of the AAA or an endoleak of the AAA. The prediction may be generated based on the voxels of the 3D segmentation(s), for example. In some embodiments, the prediction may include one or more diameters of the AAA. The diameters may be anterior-posterior diameters, such as maximum length anterior-posterior diameters. The diameters may be predicted based on the voxels of the 3D segmentation(s), for example.

As described herein at least with respect to FIG. 9, the techniques developed by the inventors include techniques for training a machine learning model to generate predictions, such as those described at least with respect to FIGS. 5-8 and 10-11.

Figure 12:
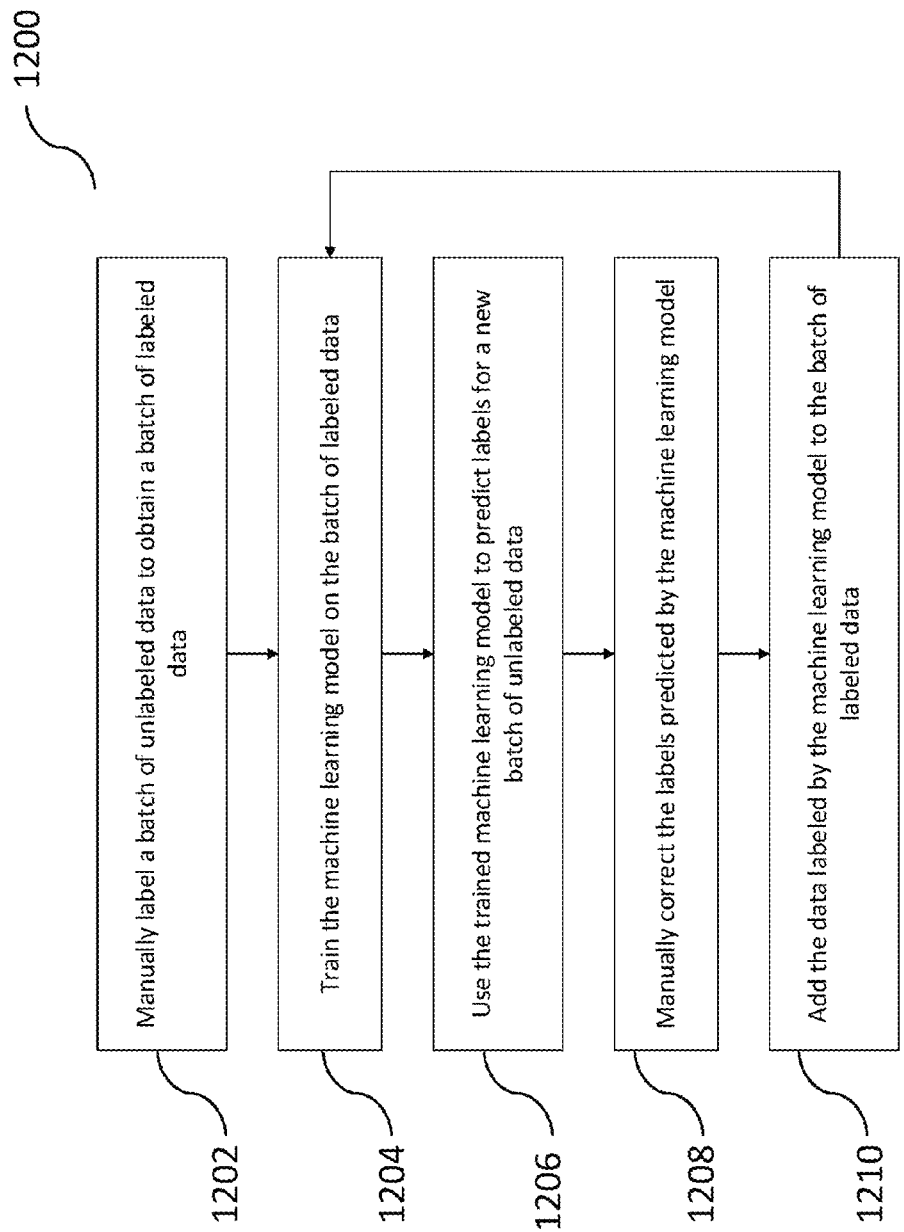
FIG. 12 is a flow diagram illustrating a semi-supervised method of labeling data, in accordance with some embodiments of the technology described herein.

FIG. 12 is a flow diagram illustrating a method 1200 for labeling training data. Steps of method 1200, including those involving use of the machine learning model, are carried out by one or more computer hardware processors.

Method 1200 may serve to reduce the time and effort associated with generating training data to train a machine learning model, by allowing some of the training data to be labeled automatically by the model itself, based on an initial set of manually-generated labels. The Method 1200 may be applied to a set of unlabeled CTA images, for example, in order to generate labeled CTA images, although method 1200 is not limited in this regard.

At block 1202, a batch of unlabeled data is manually labeled in order to obtain an initial batch of labeled data. Manually labeling the unlabeled data may include, for example, identifying a bounding box around an AAA in axial slice of input CTA images. In some embodiments, manually labeling the unlabeled data may include labeling voxels of a volume defined by multiple CTA images to indicate whether each voxel is occupied by an AAA, endograft, or endoleak. In some embodiments, only certain images slices of the volume may be labelled in this manner (e.g., 3 to 8 axial slices, 3 to 8 sagittal slices, and 3 to 8 coronal slices may be labeled). Any suitable quantity of training data may be labeled at block 1202. The labeling may be performed by any suitably-prepared individual, such as a radiologist, physician, or other expert.

At block 1204, the machine learning model is trained based on the batch of labeled data. This may include training one or more neural networks of the machine learning model, as described herein at least with respect to FIGS. 13-15. The labeled data may be split into a training set and validation set as part of training the machine learning model. If the labeled data includes CTA images, then the training set and validation set may be split such that CTA images from scans of the same patient are in the same set. The machine learning model may be trained for multiple epochs. The machine learning model may be trained using a loss function that accounts for whether particular data of the training data was labelled manually or labeled by the machine learning model. For example, a Dice loss function may be utilized that weights predictions for the manually labeled data more heavily than predictions for the machine learning model labeled data.

At block 1206, the machine learning model may be used to predict labels for a new batch of unlabeled data. This may include using particular neural networks of the machine learning model to generate corresponding labels, as described herein at least with respect to FIGS. 13-15. The labels predicted by the machine learning model at block 1206 may also be post-processed, for example to remove low-confidence predictions (e.g. any predictions with probability below 75%, below 50%, or below any other suitable threshold) or to convert the predicted labels to an appropriate format (e.g., a predicted 3D segmentation label may be clustered and converted to one or more corresponding masks, as described with respect to FIGS. 10-11).

At block 1208, the labels predicted by the machine learning model may be manually corrected. The correction may be performed by any suitably-prepared individual, such as a radiologist, physician, or other expert. Correcting the labels may include modifying or relabeling some or all of the training data. In some cases, some or all of the labels may not need to be corrected (e.g., some or all of the labels predicted by the machine learning model may be correct). In some cases, training data may be removed from the training data set if it cannot be labeled.

At block 1210, the data labeled by the machine learning model is added to the batch of labeled data. This may occur after the data labeled by the machine learning has been manually corrected as needed at block 1208. In some cases, not all of the labeled data will be incorporated into the batch of labeled data. For example, predicted labels with low-confidence, or predicted labels which were not manually reviewed and/or corrected, may be omitted from the batch of labeled data at block 1210.

As shown in FIG. 12, method 1200 includes a loop from block 1210 to block 1204. This indicates that these steps of method 1200 may be performed repeatedly, so as to produce an increasing quantity of labeled training data as the model is trained. This loop may be repeated until a desired quantity of training data has been obtained, or until there is no more unlabeled data to be labeled.

Exemplary Machine Learning Model and Training Method

Described herein is an implementation of an exemplary machine learning model and training method, according to some embodiments. The techniques described herein are not limited to this implementation. The input data set for this example is a set of CTA images, comprising CTA image slices from abdominal CTA scans of multiple patients, and may include hundreds of CTA images, thousands of CTA images, or more.

Training Bounding Box Detector

The training method begins with manually labeling a first batch of the input CTA images with bounding boxes around the abdominal aortic aneurysm (this may correspond, for example, to the localizing step described elsewhere herein). Each axial CTA image slice is labeled in this manner. Axial CTA images, in this example, are 512×512 slices.

Next, a Retina-Net neural network is trained for detecting bounding boxes. This neural network is built on the backbone of a Res-Net 50 neural network, as described herein at least with respect to FIG. 14. In this example, the Retina-Net is trained with an Adam optimizer, smooth Li regression loss, and focal classification loss. The default Retina-Net classification and regression models are employed. A batch size of six input CTA images is used. The initial learning rate is 1e-5.

In this example, the input CTA images and corresponding bounding boxes are affine transformed in order to augment the training data (e.g., the training data may be rotated, translated, reflected, and/or scaled). The Retina-Net is trained with a decaying learning rate, the learning rate decaying by half if validation loss does not improve in ten epochs of training. In this example, a validation set is defined as 20% of the full training data, and is defined such that all of a single patient's scans will be in same training or testing fold. The Retina-Net is trained in this manner for 25 epochs.

Next, the trained Retina-Net is used to predict on a new batch of input CTA images. For each axial slice with a bounding box classification probability above 0.75, the corresponding predicted bounding box is saved.

The bounding boxes are then post-processed as follows. First, find every sequential stack of axial slices with a bounding box prediction made above the threshold. Then, for each sequential stack of predictions, determine the percentage of total predictions that stack represents (e.g., for 20 predictions made, a stack of 5 sequential predictions is 25%). Next, remove all stacks of sequential predictions with under 20%. For all those stacks with predictions between 20% and 50%, if another stack of sequential predictions is within 3 slices in either direction, and if that stack is >20%, keep both stacks and fill the slices in between with copies of the closest bounding box axially. For all those stacks with predictions between 20% and 50%, if another valid stack is not within 3 slices, delete the stack. Keep the remaining predictions. If no predictions remain, then repeat the above steps but with 1% less on each threshold (e.g., under 19% and between 19% and 49%, et cetera). Continue until the above steps result in at least one predicted bounding box remaining.

Next, the predicted bounding boxes are manually corrected (e.g., as described herein at least with respect to FIG. 12), and the Retina-Net is re-trained with the now larger data set. This process is repeated until either the Retina-Net achieves a desired performance, or until there are no new scans for which to produce bounding boxes.

Figure 13:
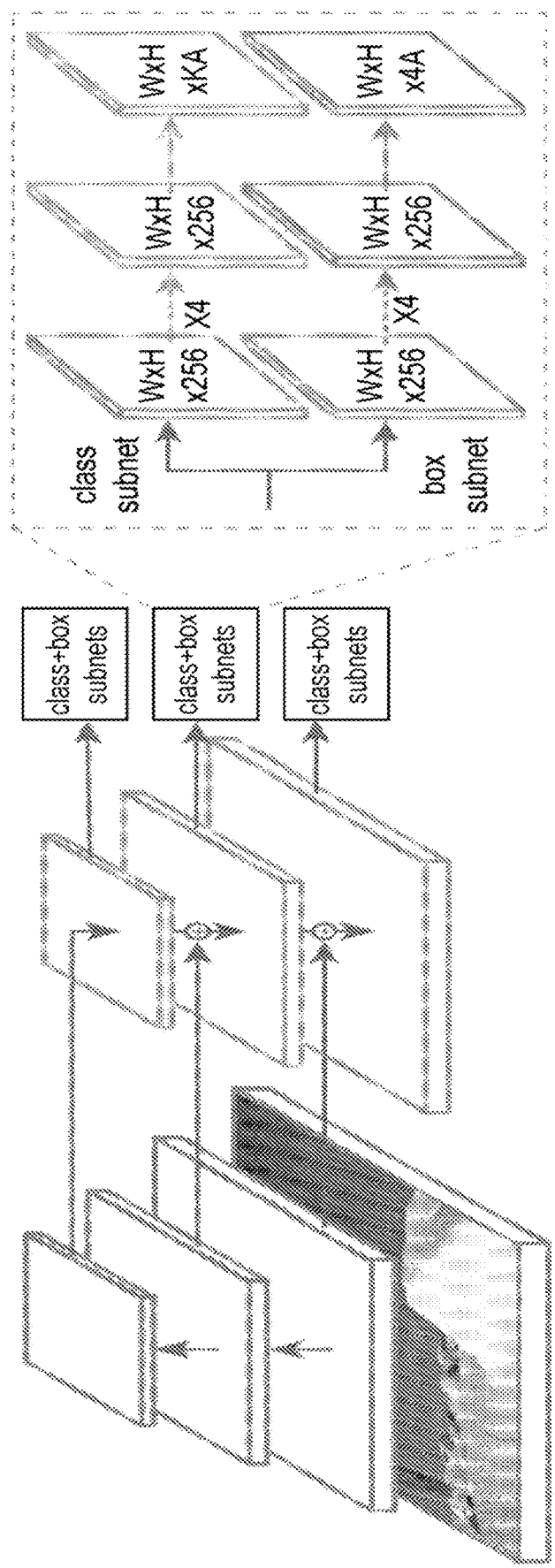
FIG. 13 illustrates an exemplary Retina-Net neural network, in accordance with some embodiments of the technology described herein.

FIG. 13 illustrates an exemplary Retina-Net neural network. Details of the implementation of this neural network are given in the paper titled "Focal Loss for Dense Object Detection" by Tsung-Yi Lin, Priya Goyal, Ross Girshick, Kaiming He, and Piotr Dollar of Facebook AI Research (FAIR), February 2018 (https://arxiv.org/abs/1708.02002), which is hereby incorporated by reference in its entirety.

Training Binary Endoleak Classifier

In this example, the input for training the binary endoleak classifier includes: the input CTA images, the bounding box locations for AAA, and the ground truth labels indicating, for each axial slice of the input CTA images, whether or not an endoleak is present.

In this example, the ground truth labels for the classifier are generated as follows. The case reports for each CTA scan comprising the CTA images are downloaded, and then text-mined to semi-automatically determine if each scan had an endoleak or not, and further what type of endoleak, and, if mentioned, the axial slices in which the endoleak can be seen. Further, the endoleak positive cases and 10% of the endoleak negative cases were manually reviewed, as were the axial slice in which it was recorded that the endoleak can be seen. In this example, ground truth labels indicating in which axial slices an endoleak can be seen were thus generated from these two sources.

Figure 14:
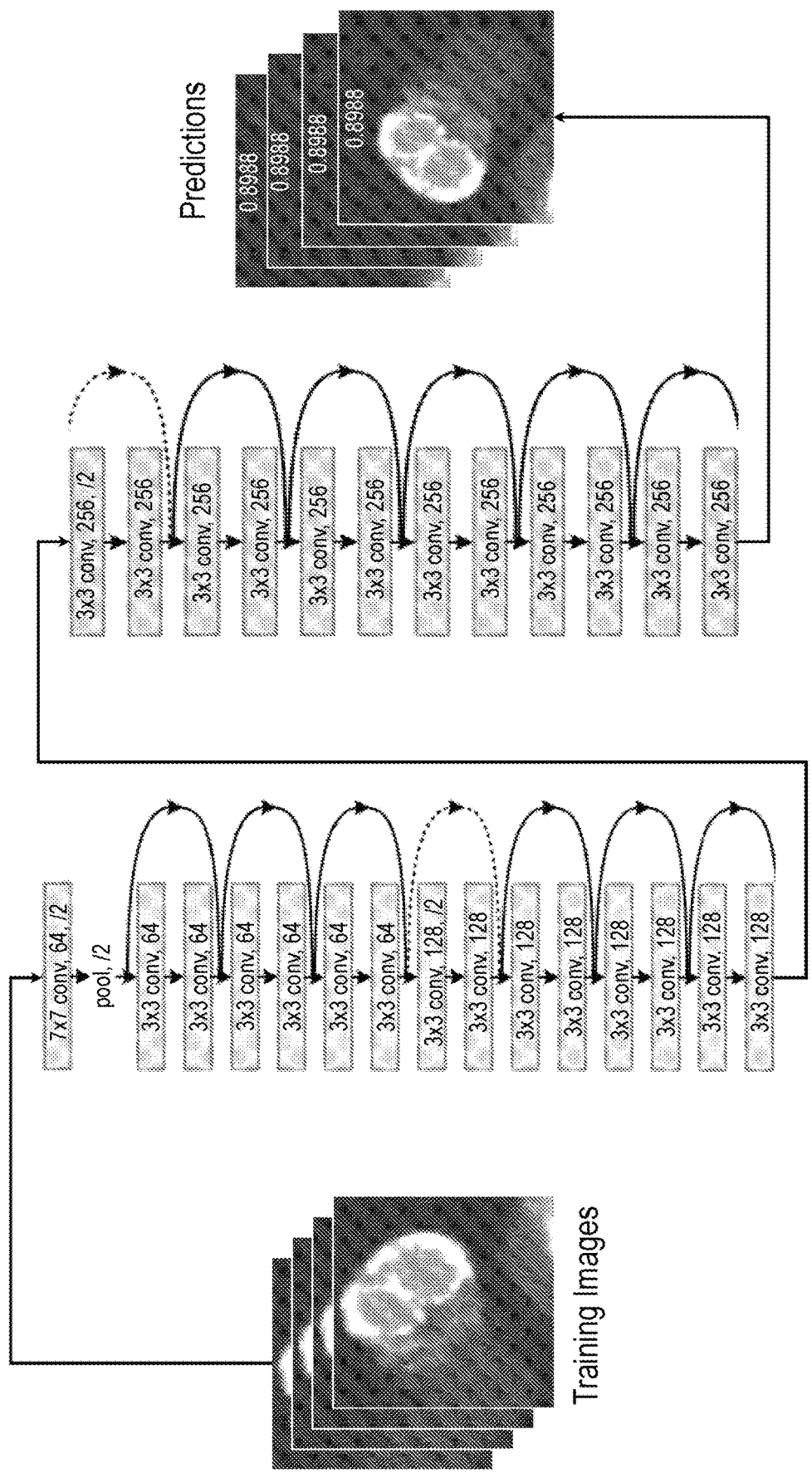
FIG. 14 illustrates an exemplary modified Res-Net 50 neural network, in accordance with some embodiments of the technology described herein.

Next, a neural network built on the backbone of a Res-Net 50 neural network is trained for the task of binary endoleak classification based on these inputs. FIG. 14 illustrates an exemplary modified Res-Net 50 neural network. Details of the implementation of this neural network are given in the paper titled "Deep Residual Learning for Image Recognition" by Kaiming He, Xiangyu Zhang, Shaoqing Ren, and Jian Sun of Microsoft Research, December 2015 (https://arxiv.org/abs/1512.03385), which is hereby incorporated by reference in its entirety. As shown in FIG. 14, the neural network in this example is a modified Res-Net 50 model, with the last convolution block and identity block removed.

In this example, a five-fold cross validation (respecting scans from each patient, such that they are in the same training/testing fold) is used. The training set is further broken down into 90% for training, 10% for internal validation. Then, the model based off Res-Net 50 is trained. Each input image, representing an axial slice of the AAA, is scaled to 128×128, where, if the bounding AAA box is too large, the image is down-sampled to be 128×128, and if the bounding AAA box is too small, the crop around the AAA is expanded to be 128×128. The model is trained with a binary cross entropy loss function, for 150 epochs using snapshot ensembling, wherein cyclic learning rate decay is applied, with a starting learning rate of 0.01, in order to build 3 model snapshots (after 50 epochs each) using stochastic gradient descent optimization. At test time, the predictions from an ensemble of these 3 saved weights is used.

In this example, the modified Res-Net 50 is trained with a number of different data augmentation techniques (only applied to the training set). Before the processing to ensure the image is 128×128 occurs, as an optional training data augmentation step, the AAA bounding box is padded in random directions, random rotation of the image is performed, random translation is performed, random shearing is performed, and/or random scaling is performed.

The modified Res-Net 50 is then used to predict on the pre-contrast axial CTA image slices for all available CTA scans without endoleak labels. Since an endoleak will not be visible in pre-contrast scans, every endoleak positive prediction made on this set is known to be a false positive. In this case, it is important that pre-contrast scans for the training set are already present, and no pre-contrast scans from subjects present in either the validation or the testing fold are selected. All false positive predictions made are then used to supplement the training set, and all steps besides this one are repeated, effectively retraining the model with additional, potentially helpful training data.

Next, the modified Res-Net 50 is used to predict on the left out testing fold. Predictions are combined to form an overall prediction for each CTA scan as follows. First, the predictions (i.e., a binary classification of yes/no endoleak, or a score between 0 and 1) on all venous and arterial phase axial slices of that scan are considered (not including the pre-contrast), and if only one of arterial or venous phase is available, only the one phase is used. In this example, the maximum prediction made across the considered slices is associated with the CTA scan. In order to discretize the predictions into an overall binary classification, a threshold (i.e., above which the classification is considered 1 and below which the classification is considered 0) is determined as the value which maximizes the F1 score on the training set. Finally, five-fold validation summary statistics are reported as the average value obtained on the validation set of each fold.

Training 3D Segmentation

In this example, the input data for the 3D segmentation network for each CTA scan is a three-dimensional volume (referred to herein as a 3D bounding box) extracted from the CTA scan, generated based on the AAA bounding box predictions for the individual axial image slices of the CTA scan. Since the predicted bounding boxes around the AAA may vary in size in each image slice, and 3D neural networks (such as the 3D U-Net neural network used in this example) require a fixed input size, a 128×128×128 3D bounding box around the AAA is determined as follows.

First, a base 3D bounding box is calculated from each of the images slices as the maximum/minimum predicted bounding box corners in all three dimensions. This produces a base 3D bounding box which contains all of the 2D bounding boxes from the individual image slices. Next, an axial padding, defined as the thickness of the axial slice in millimeters times seven, rounded to integer, is applied to both axial dimensions, thereby enlarging the base 3D bounding box. Then, any dimensions which are under 128 are padded to 128. If any dimension is over 128, then the larger, expanded bounding box is applied to the original base bounding box, and this volume then 3D down-sampled to have dimensions 128×128×128, and the resulting affine is saved.

In this example, the 3D segmentation network is being trained to segment AAA and endograft within each 3D bounding box. The following process is used to sparsely label the 128×128×128 3D bounding boxes for the two classes (AAA and endograft). First, in each dimension (axial, sagittal, coronal), label 3 to 8 slices manually for presence of the classes. Further, once labeled, create a mark on that slice indicating (1) that it has been "seen", and (2) which dimension it is in (e.g., axial if axial, et cetera). Further, ensure that the first and last slice across all three dimensions where the AAA or endograft can be seen is labeled. Next, create a "seen" binary mask for each sparsely labeled image, including all slices which have been marked "seen", and further all slices around the "seen" slices, since it may be assumed these slice contain neither AAA nor endograft, given the rule above regarding labeling the first/last slice where the AAA or endograft can be seen in each dimension. In this example, the "seen" binary mask will be passed along with the corresponding 3D bounding box and the 3D multi-class segmentation mask, as another 3D binary volume, and used with the loss function to only compute the loss function on seen voxels, despite the neural network receiving the full volume and making predictions on the full volume.

Figure 15:
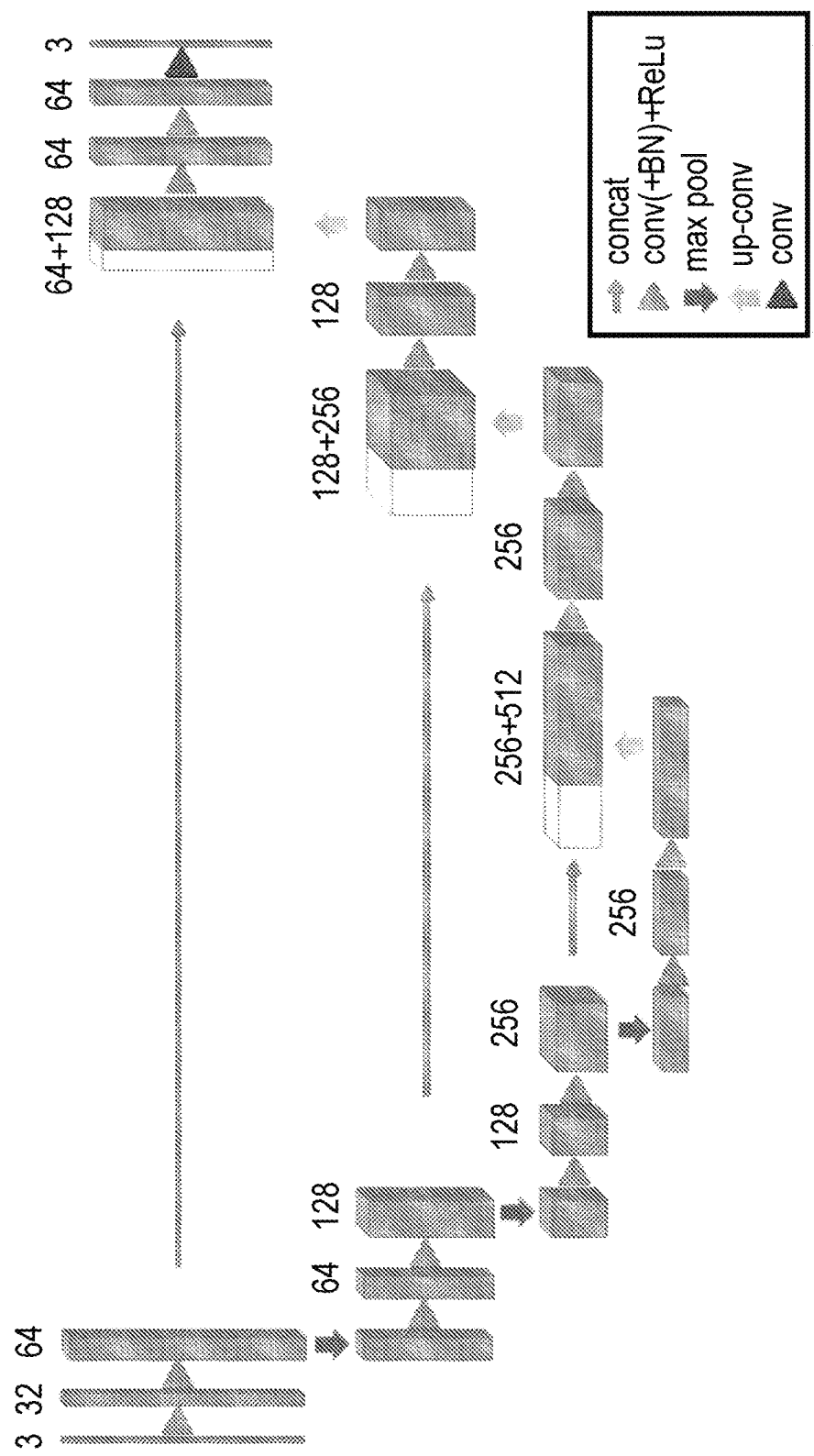
FIG. 15 illustrates an exemplary 3D U-Net neural network, in accordance with some embodiments of the technology described herein.

In this example, a 3D U-Net neural network is trained for the task of 3D segmentation. FIG. 15 illustrates an exemplary 3D U-Net neural network. In this case, the 3D U-Net is configured with 16 base filters, 5 layers deep, with a dropout of 0.3, sigmoid final activation layers, and 4 segmentation levels. A batch size of 6 is used, and the neural network is trained with five snapshots over 100 epochs.

For the loss function, a custom multi-class Dice loss function is utilized to account for the sparse labeling technique described above. In this particular case, the Dice loss function is calculation according to the formula:

$$Loss = \frac{\forall i \in |classes| \frac{2 * \Sigma \, True_i \cap Pred_i}{\Sigma \, True_i + \Sigma \, Pred_i \cap Seen}}{|classes|}$$

where classes refers to the different input classes (AAA and endograft), "seen" refers to a binary mask indicating whether that voxel was seen while performing partial segmentation (i.e., sparse labeling), and $True_i$ and $Pred_i$ refer to the ground truth label and predicted label for class i.

Next, the trained 3D U-Net is used to predict on a set of new 3D bounding boxes. Predictions from the 3D U-Net are post-processed as follows. First, the predictions are represented as a 2×128×128×128 volume, where the first dimension contains a probability that voxel is part of an AAA and endograft respectively. The predictions are first set as the average of each of the five model snapshot predictions. Next, all probabilities under 0.5 are set to be 0. Then, a single 128×128×128 mask is created, where: if both AAA and endograft predictions have been set to 0 (i.e., they were both under 0.5), the voxel is set to 0; if AAA is predicted at higher probability than endograft, the voxel is set to 1; and if endograft is predicted at higher probability than AAA, the voxel is set to 2. Define a "total size" of the predictions as the sum of voxels predicted 1 or 2 (AAA endograft). Then, compute all connected 3D clusters with the same label (excluding background, i.e., just for AAA and endograft labels), and for each cluster, do the following.

First, if the size of the cluster (i.e., the sum of the connected voxels, in 3D space, such that each voxel has 8 neighbors) divided by the "total size" of the predictions is greater than 0.01 (i.e., if this cluster makes up more than 1 percent of the predictions), keep the cluster as is. Otherwise, if it makes up less than 1 percent of the predictions, set all member voxels of the cluster to the most present class in the voxels surrounding that cluster. That is, compute all voxels on the boundary of the cluster, and then compute the most dominant label among those, and set the members of the cluster equal to that label.

After completing this process for each cluster, reshape the 2×128×128×128 volume into two binary 128×128×128 segmentation masks for each class, AAA and endograft, and return.

The trained 3D U-Net is then used to predict on new volumes. The predictions on the new volumes are manually corrected and used as ground truth 3D multi-class (AAA and endograft) segmentations. Finally, five-fold cross validation metrics are generated by performing a five-fold cross validation (keeping scans from each patient together, as before), and averaging metrics computed on the validation folds.

Extract Volume and Maximum Anterior-Posterior Diameters

In order to extract volume and diameter information (here, maximum anterior-posterior diameters), begin by resampling the 3D segmentations into voxel space, using the saved affine, such that each voxel in the 3D segmentations represents, in the real world, a volume of scan thickness times the pixel dimensions in millimeters.

Volume can then be calculated as follows. For each of the combined AAA and endograft segmentation, the AAA segmentation alone, and the endograft segmentation alone, calculate the volume as the sum of the voxels times the scan thickness times each pixel dimension in millimeters.

Maximum anterior-posterior diameters can then be calculated as follows. First, combine the AAA and endograft segmentations into a single binary mask representing either AAA or endograft. For each axial slice, do as follows. First, determine the points on the outer edge of segmentation. If the slice has at least 10 edge points, continue, otherwise skip this slice. Next, determine the two points from the edge points with the largest distance in millimeters between them (e.g., by calculating the distance for every pairwise set of points, and taking the maximum). Then, determine the two points closest to the real perpendicular line between the two points with the largest distance in mm between them (e.g., by first calculating the real perpendicular line, and then finding the voxels which come closest to intersecting with that line). Once this has been done for each axial slice, sum the distances of the lines of each slice (i.e., the maximum distance between two points, and its perpendicular line). Then, select the slice with the highest summed anterior-posterior, and set the length of the two lines equal to the predicted maximum anterior-posterior for the full scan.

Endoleak Segmentation

In this example, predicting a 3D segmentation of an endoleak in the CTA images may proceed in the same manner as the 3D segmentation example above, with the following differences. First, there is only one class (endoleak), and the steps indicated above proceed mutatis mutandis. Additionally, in this example, the endoleaks are not sparsely labeled, but rather manually densely segmented (i.e., the voxels containing endoleak manually identified).

In some embodiments, a 3D segmentation of an endoleak may be used to provide predictions regarding the volume or diameter(s) of the endoleak. This may be done, for example, as described above with respect to AAA volume/diameter(s), mutatis mutandis.

Results

AAA Localization

An exemplary AAA localization network, implemented according to techniques described herein, had an accuracy of 98.7% in capturing the AAA within the region of interest on the CTA image. This estimation of accuracy was based on manual review and correction of 314 previously unseen scans that were supplied to the localization network. These scans were composed of 91,575 axial slices, of which 412 (0.4%) required minor manual operator revision, defined as small changes made to a bounding box or to a slice missed before or after the predicted aneurysm region. These revisions may be caught by automated padding. Only two predicted slices with a more significant bounding box error were observed. A significant number of AAA predictions were missed altogether on only four full scans.

Endoleak Binary Classification

Figure 16A:
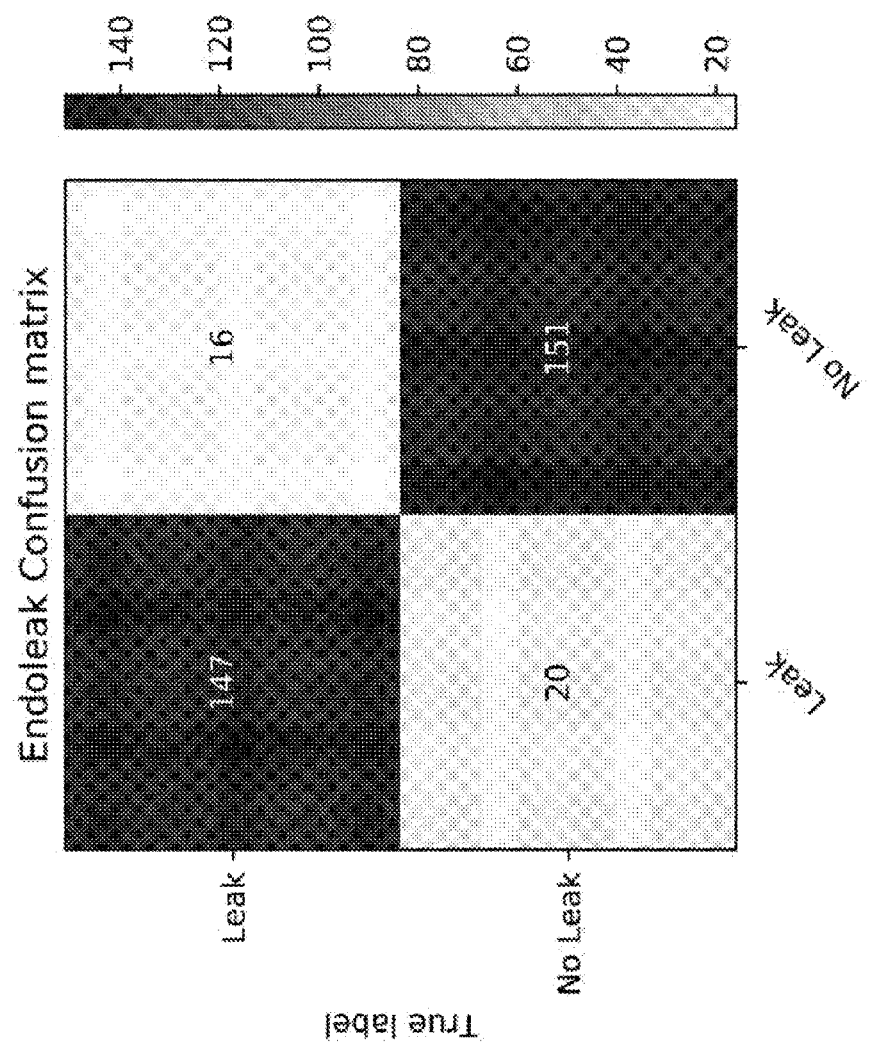
FIGS. 16A-B are charts showing exemplary results of machine learning model(s) trained for diagnosing endoleaks, in accordance with some embodiments of the technology described herein.
Figure 16B:
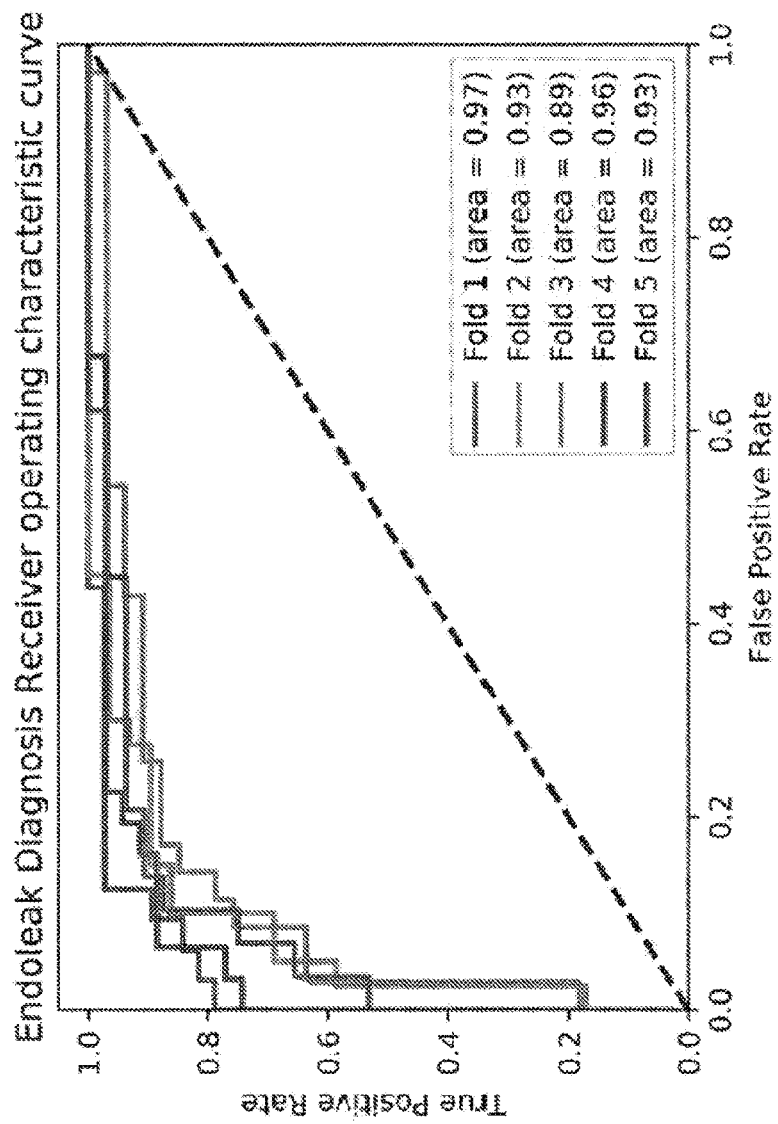

FIGS. 16A-B are charts showing exemplary results of machine learning model(s) trained for diagnosing endoleaks. In particular, FIG. 16A is an endoleak confusion matrix for a machine learning model trained to detect endoleaks, according to the techniques described herein. The endoleak confusion matrix depicts true and false positives and negatives for the binary endoleak detection task. FIG. 16B a receiver operating characteristic curve for a machine learning model trained to detect endoleaks, according to the techniques described herein. Computed across fivefold cross-validation, the binary classification machine learning model correctly identified the presence of an endoleak in 147 of 167 scans. Absence of endoleak was correctly reported in 151 of 167 scans. The resulting sensitivity and specificity for endoleak detection were 90% and 88%, respectively, with an accuracy of 89% (FIG. 16A). The positive and negative predictive values were 89% and 91%, respectively. The area under the receiver operating characteristic curves per validation fold were between 0.89 and 0.97, with an average of 0.94±0.03 (FIG. 4).

Segmentation

FIG. 17 is a chart showing exemplary results of machine learning model(s) trained for predicting AAA/endograft 3D segmentations, according to the techniques described herein. As determined by cross-validated performance on 33 fully segmented scans, the machine learning model accurately segmented the AAA with a Dice coefficient of 91%±5% and intersection over union of 84%±9% (FIG. 17). The accuracy of endograft segmentation was higher with a Dice coefficient of 95%±3% and intersection over union of 90%±5%.

AAA Diameter

Figure 18A:
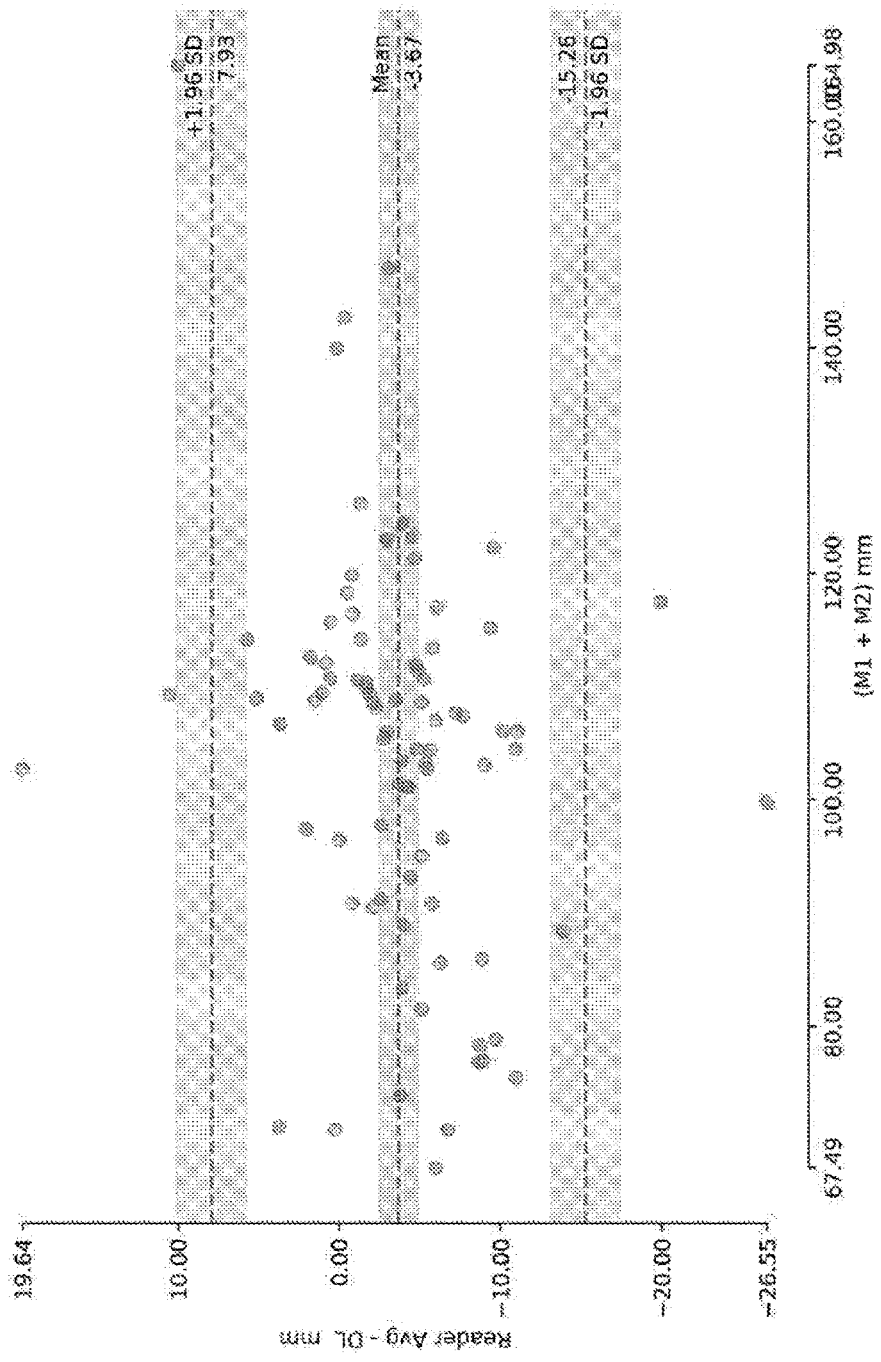
FIGS. 18A-C are charts showing exemplary results of machine learning model(s) trained for predicting AAA diameter, in accordance with some embodiments of the technology described herein.
Figure 18B:
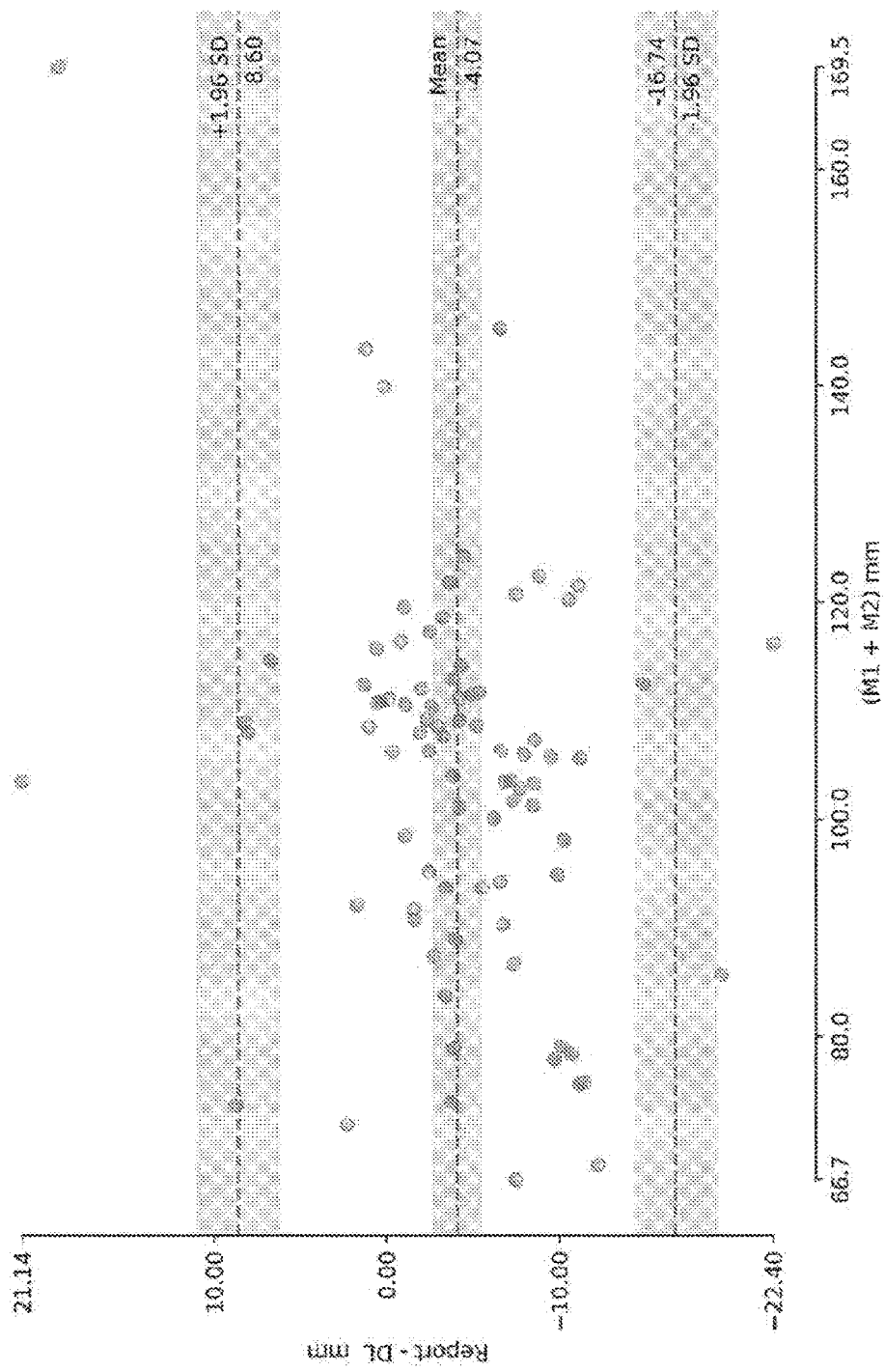
Figure 18C:
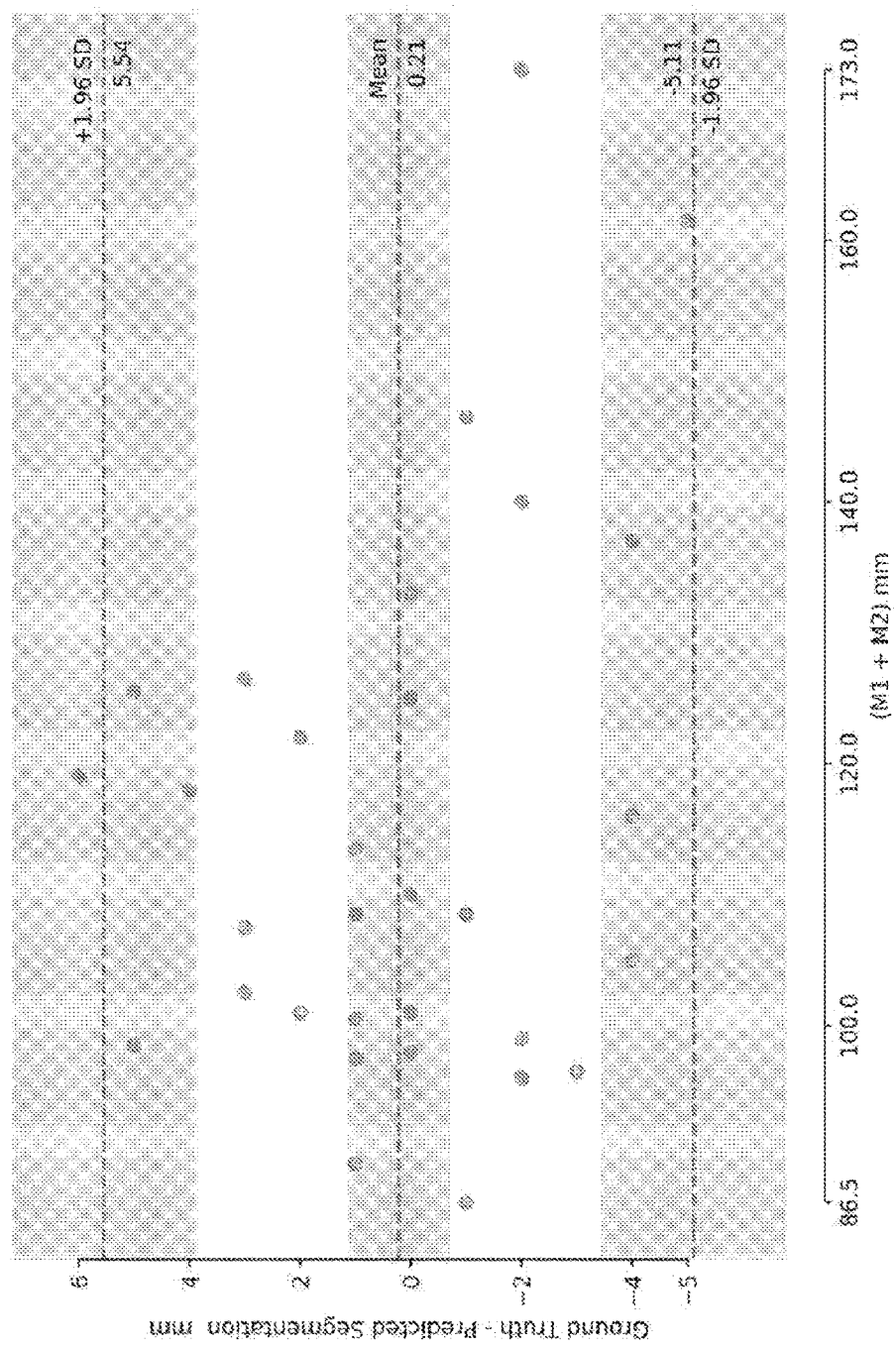

FIGS. 18A-C are charts showing exemplary results of machine learning model(s) trained for predicting AAA diameter, according to the techniques described herein. In particular, FIGS. 18A-C are Bland-Altman plots of AAA diameter measurements (sum of both maximal measurement M1+M2) that compare the machine learning model results (marked "DL" in FIGS. 18A-C).

In FIGS. 18A and 18B, the machine learning model predictions of maximum diameter in two directions are compared with official radiology reports that listed both maximal AAA diameter (FIG. 18B), as well as with an average maximal AAA diameter as reported by two expert readers (FIG. 18A). In comparing the average of two readers with the machine learning model predictions, the coefficient of repeatability was 13.72 (FIG. 18A). In comparing the radiology report with the machine learning model predictions, the coefficient of repeatability was 15.06 (FIG. 18B).

In FIG. 18C, the results of the algorithm for extracting maximal diameter from a segmentation (described herein at least with respect to the section titled "Extract volume and maximum anterior-posterior diameters" above) are compared for 33 fully segmented scans. In particular, the results are compared between the algorithm for extracting maximal diameter applied to a manually-labeled ground truth segmentation, and the same algorithm applied to a machine learning model predicted segmentation, with a coefficient of repeatability of 5.42.

AAA and Endoleak Volume

The performance of an exemplary machine model, implemented according to techniques described herein, was evaluated for the AAA volume measurement task on the 33 fully segmented scans with fivefold cross-validation, in which all partial segmentations were included within the training set within all folds. The machine learning model obtained a Dice coefficient of 91%±5% for AAA volume with a 4.5±3.4 mm3 absolute volume error. The network obtained a Dice coefficient of 91%±5% for predicting endograft volume with a 5.2 6 6.7 mm3 absolute volume error.

For the endoleak volume measurement task, an exemplary machine learning model implemented according to techniques described herein obtained a Dice coefficient of 0.53±0.2 and an average error of 1.2 6±1.9 mL.

Computer Implementation and Technical Improvements

Figure 19:
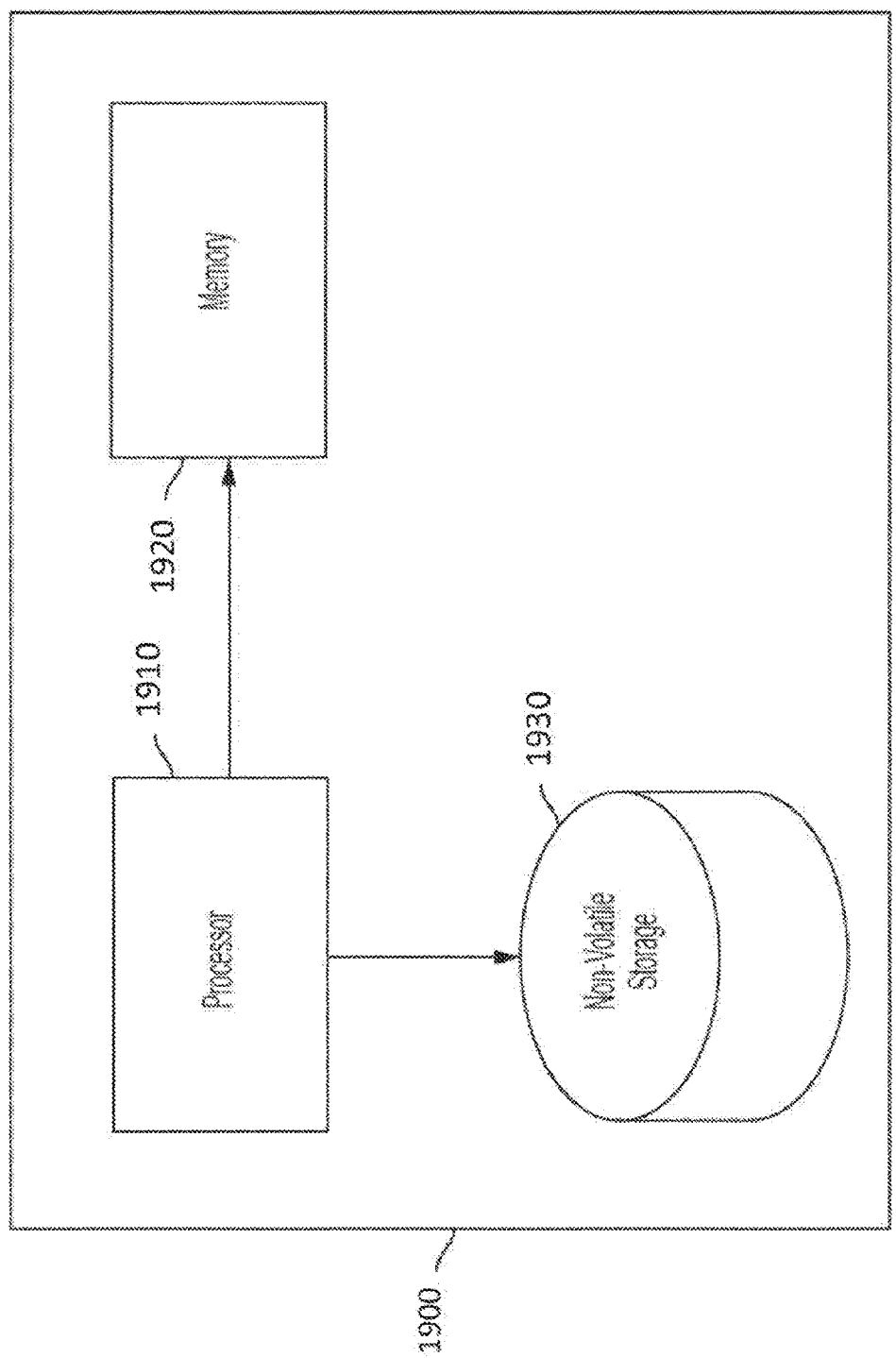
FIG. 19 is a block diagram of an illustrative computer system that may be used in implementing some embodiments of the technology described herein.

An illustrative implementation of a computer system 1900 that may be used in connection with any of the embodiments of the disclosure provided herein is shown in FIG. 19. The computer system 1900 may include one or more processors 1910 and one or more articles of manufacture that comprise non-transitory computer-readable storage media (e.g., memory 1920 and one or more non-volatile storage media 1930). The processor(s) 1910 may control writing data to and reading data from the memory 1920 and the non-volatile storage device 1930 in any suitable manner, as the aspects of the technology described herein are not limited in this respect. To perform any of the functionality described herein, the processor(s) 1910 may execute one or more processor-executable instructions stored in one or more non-transitory computer-readable storage media (e.g., the memory 1920), which may serve as non-transitory computer-readable storage media storing processor-executable instructions for execution by the processor(s) 1910.

The terms "program" or "software" are used herein in a generic sense to refer to any type of computer code or set of processor-executable instructions that can be employed to program a computer or other processor to implement various aspects of embodiments as described herein. Additionally, in some embodiments, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

In some embodiments, a machine learning model as described herein may be stored in one or more non-transitory computer-readable storage media in any suitable form. The techniques described herein for training and using the machine learning may include accessing and/or modifying a representation of a machine learning model stored in the one or more non-transitory computer-readable storage media (e.g., to update weights associated with the machine learning model, to store the trained machine learning model, or to retrieve the trained machine learning model for use). In some embodiments, techniques described herein involving providing data (e.g., CT image data) to a machine learning model as input may include executing instructions (e.g., of a program) with at least one processor that cause the processor to access the data from a location in the one or more non-transitory storage media and provide the data as input to the machine learning model.

Also, various inventive concepts may be embodied as one or more processes, of which examples have been provided including with reference to FIGS. 5-12. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

As described below and elsewhere herein (e.g., in the Results section above), the techniques discovered by the inventors provide significantly improved techniques for determining diagnoses, prognoses, and treatments for abdominal aortic aneurysms (AAAs) and related conditions (such as endoleaks). For example, the techniques described herein can provide accurate predictions of AAA and/or endoleak volume and diameter. These metrics can be utilized to greatly improve the effectiveness and efficiency of clinical follow-up and decision-making for AAA and/or endoleak treatment. Relatively small changes in AAA and/or endoleak diameter can be associated with substantial changes in volume, and so accurate predictions of both metrics can improve the robustness and accuracy of diagnosis, prognosis, and treatment for these conditions.

Another advantage of the techniques discovered by the inventors is that review of prior imaging for comparison purposes can be significantly expedited using a machine learning model according to the techniques described herein, thus improving the speed, ease, and rigor of follow-up. Comparisons of endoleak volume, AAA diameter, and AAA volume can be performed by a computer hardware processor embodying a machine learning model as described herein, providing physicians and other experts with valuable information that would infeasible or outright impossible for them to obtain manually. For example, some parameters relating to AAAs, such as endoleak volume, are not readily available from CT scans using conventional techniques. The techniques described herein can provide these parameters, with great efficiency and minimal human effort, thereby providing a significant improvement over conventional techniques.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "substantially", "approximately", and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A method for diagnosing a patient having an abdominal aortic aneurysm (AAA), the method comprising:
   using at least one computer hardware processor to perform:
      accessing computed tomography angiography (CTA) images of a portion of the patient, the portion of the patient including the AAA of the patient following endovascular AAA repair (EVAR);
      providing the CTA images as input to a trained machine learning model, the trained machine learning model being configured to classify a property of the AAA based on the CTA images; and
      determining, based on the classified property of the AAA, a diagnosis of the patient, the diagnosis comprising information identifying at least one condition of the patient used as a prognostic indicator of an AAA rupture.

2. The method of claim 1, wherein classifying the property of the AAA comprises predicting a location of the AAA in the input CTA images.

3. The method of claim 1, wherein classifying the property of the AAA comprises predicting a presence or absence of an endoleak in the input CTA images.

4. The method of claim 1, wherein classifying the property of the AAA comprises predicting a three-dimensional (3D) segmentation of the AAA in the input CTA images.

5. The method of claim 1, wherein classifying the property of the AAA comprises predicting a three-dimensional (3D) segmentation of an endograft in the input CTA images.

6. The method of claim 1, wherein classifying the property of the AAA comprises predicting a three-dimensional (3D) segmentation of an endoleak in the input CTA images.

7. The method of claim 1, wherein classifying the property of the AAA comprises predicting a diameter of the AAA in the input CTA images.

8. The method of claim 1, wherein classifying the property of the AAA comprises predicting a volume of the AAA in the input CTA images.

9. The method of claim 1, wherein classifying the property of the AAA comprises predicting a volume of an endoleak in the input CTA images.

10. The method of claim 1, wherein the trained machine learning model comprises a neural network model.

11. The method of claim 10, wherein the neural network model was trained using a dice loss function.

12. The method of claim 10, wherein the condition of the patient identified by the diagnosis is an endoleak of the AAA.

13. The method of claim 10, wherein the neural network model includes one or more convolutional layers.

14. The method of claim 10, wherein the neural network model was trained using a training dataset comprising a set of training CTA images.

15. The method of claim 14, wherein the training CTA images comprise postoperative CTA images.

16. The method of claim 14, wherein the training CTA images comprise CTA images having multiple contrast phases.

17. The method of claim 1, wherein diagnosis identifies a severity of the condition.

18. The method of claim 1, further comprising determining, based on the classified property of the AAA, the treatment for the patient, the treatment comprising information indicating a clinical course of action to be taken in response to a condition of the patient.

19. A system, comprising:
- at least one computer hardware processor; and
- at least one non-transitory computer-readable storage medium storing processor-executable instructions that, when executed by the computer hardware processor, cause the computer hardware processor to perform a method for diagnosing a patient having an abdominal aortic aneurysm (AAA), the method comprising:
  - accessing computed tomography angiography (CTA) images of a portion of the patient, the portion of the patient including the AAA of the patient following endovascular AAA repair (EVAR);
  - providing the CTA images as input to a trained machine learning model, the trained machine learning model being configured to classify a property of the AAA based on the CTA images; and
  - determining, based on the classified property of the AAA, a diagnosis of the patient, the diagnosis comprising information identifying at least one condition of the patient used as a prognostic indicator of an AAA rupture.

20. At least one non-transitory computer-readable storage medium storing processor-executable instructions that, when executed by a computer hardware processor, cause the computer hardware processor to perform a method for diagnosing a patient having an abdominal aortic aneurysm (AAA), the method comprising:
- accessing computed tomography angiography (CTA) images of a portion of the patient, the portion of the patient including the AAA of the patient following endovascular AAA repair (EVAR);
- providing the CTA images as input to a trained machine learning model, the trained machine learning model being configured to classify a property of the AAA based on the CTA images; and
- determining, based on the classified property of the AAA, a diagnosis of the patient, the diagnosis comprising information identifying at least one condition of the patient used as a prognostic indicator of an AAA rupture.

* * * * *